United States Patent
Manchekar et al.

(10) Patent No.: US 10,155,709 B2
(45) Date of Patent: Dec. 18, 2018

(54) SYTHESIS OF BISPHENOLS

(71) Applicant: SABIC GLOBAL TECHNOLOGIES B.V., Bergen op Zoom (NL)

(72) Inventors: Arun Vasant Manchekar, Bangalore (IN); Samir Anapat, Bangalore (IN); Martin Oyevaar, Goes (NL)

(73) Assignee: SABIC GLOBAL TECHNOLOGIES B.V., Bergen Op Zoom (NL)

(*) Notice: Subject to any disclaimer, the term of this patent is extended or adjusted under 35 U.S.C. 154(b) by 0 days.

(21) Appl. No.: 15/325,333

(22) PCT Filed: Jul. 14, 2015

(86) PCT No.: PCT/IB2015/055336
§ 371 (c)(1),
(2) Date: Jan. 10, 2017

(87) PCT Pub. No.: WO2016/009362
PCT Pub. Date: Jan. 21, 2016

(65) Prior Publication Data
US 2017/0174598 A1    Jun. 22, 2017

Related U.S. Application Data

(60) Provisional application No. 62/024,574, filed on Jul. 15, 2014.

(51) Int. Cl.
C07C 39/16 (2006.01)
C07C 37/20 (2006.01)
B01D 3/00 (2006.01)

(52) U.S. Cl.
CPC .............. C07C 39/16 (2013.01); B01D 3/009 (2013.01); C07C 37/20 (2013.01); Y02P 20/127 (2015.11)

(58) Field of Classification Search
CPC ................................ C07C 39/16; C07C 37/20
See application file for complete search history.

(56) References Cited

U.S. PATENT DOCUMENTS 4,053,522 A * 10/1977 McClure ................. C07C 37/20
568/727
4,391,997 A    7/1983 Mendiratta
(Continued)

FOREIGN PATENT DOCUMENTS

EP        0770590 A1    5/1997
EP       11060229 A1   12/2001
(Continued)

OTHER PUBLICATIONS

International Search Report for International Application No. PCT/IB2015/055 36; International Filing Date: Jul. 14, 2015; dated Nov. 12, 2015; 6 Pages.
(Continued)

Primary Examiner — Medhanit W Bahta
(74) Attorney, Agent, or Firm — Cantor Colburn LLP

(57) ABSTRACT

Various embodiments disclosed relate to methods and apparatus for synthesizing various biphenols. In various embodiments, the present invention provides a method of making a bisphenol including feeding a phenol at or proximate to the first end of a reactor column including a first end and a second end and including a solid catalyst distributed in multiple locations between the first end and the second end of the reactor column. The method includes feeding an oxomethylene compound to the reactor column at a first location that is at or proximate the first end and at one or more additional locations between the first location and the second end of the reactor column, and removing at least some water from the reactor column. The method includes removing a product composition including a diphenolmethylene product at or proximate to the second end of the reactor column.

18 Claims, 5 Drawing Sheets

(56) References Cited

U.S. PATENT DOCUMENTS

| | | | |
|---|---|---|---|
| 4,400,555 | A | 8/1983 | Mendiratta |
| 4,590,303 | A | 5/1986 | Mendiratta |
| 5,087,767 | A | 2/1992 | Okamoto et al. |
| 5,648,561 | A | 7/1997 | Tan et al. |
| 5,679,312 | A * | 10/1997 | Jin .................. B01D 3/009 202/158 |
| 6,288,284 | B1 | 9/2001 | Eek et al. |
| 6,414,199 | B1 | 7/2002 | Saruwatari |
| 6,933,416 | B2 | 8/2005 | Chiang et al. |
| 6,939,994 | B1 | 9/2005 | Smith, Jr. et al. |
| 2004/0019241 | A1 | 1/2004 | Chiang et al. |
| 2004/0068085 | A1 | 4/2004 | Belfadhel et al. |
| 2005/0004406 | A1 | 1/2005 | Carvill et al. |
| 2008/0091051 | A1 | 4/2008 | Hong et al. |

FOREIGN PATENT DOCUMENTS

| | | |
|---|---|---|
| EP | 1669339 A1 | 6/2006 |
| EP | 2090562 A1 | 8/2009 |
| WO | 0419302 A1 | 9/1994 |
| WO | 9734688 A1 | 9/1997 |
| WO | 2004013075 A1 | 2/2004 |
| WO | 2006008230 A1 | 1/2006 |

OTHER PUBLICATIONS

Taylor et al., "Modelling reactive distillation," Chemical Engineering Science 55 (2000) pp. 5183-5229.
Written Opinion of the International Searching Authority for International Application No.: PCT/IB2015/055336; International Filing Date: Jul. 14, 2015; dated Nov. 12, 2015; 7 Pages.

* cited by examiner

SYTHESIS OF BISPHENOLS

CROSS REFERENCE TO RELATED APPLICATIONS

This application is a 371 of International Application No. PCT/IB2015/055336, filed Jul. 14, 2015, which claims priority to U.S. Application No. 62/024,574, filed Jul. 15, 2014 which are incorporated herein by reference in their entirety.

BACKGROUND OF THE INVENTION

Bisphenols are useful and important monomers for the manufacture of various polymers and resins, including curable resins. For example, bisphenol A (4,4'-(propane-2,2-diyl)diphenol, "BPA") is used for the synthesis of polymers and resins such as polycarbonates, polyamides, polyetherimides, polyarylates, epoxy resins and modified phenol-formaldehyde resins. The process for manufacturing of BPA involves synthesis of BPA and subsequent purification of the reaction mixture. BPA is synthesized by the exothermic liquid phase condensation reaction of phenol and acetone in the presence of acidic catalyst, optionally with a promoter, as shown in the scheme below.

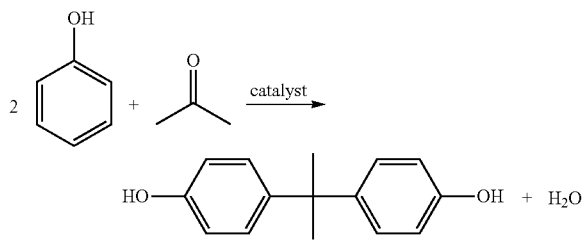

Generally BPA synthesis is performed in a shallow packed bed reactor. Temperature control in the reactor is difficult. The water produced during the synthesis is removed using an additional time-consuming and expensive dehydration step.

SUMMARY OF THE INVENTION

In various embodiments, the present invention provides methods of making a bisphenol, and apparatus for making bisphenol.

In an embodiment, a method of making a bisphenol, can comprise: feeding phenol at or proximate to the first end of a reactor column comprising a first end and a second end, the reactor column comprising a solid catalyst distributed in multiple locations between the first end and the second end of the reactor column; feeding oxomethylene compound to the reactor column at a first location that is at or proximate the first end and at one or more additional locations between the first location and the second end of the reactor column; contacting the phenol and the oxomethylene compound in the reactor column in the presence of the catalyst sufficiently to condense the phenol and oxomethylene compound to give a diphenolmethylene product and water; removing water (e.g., at least some of the water) from the reactor column by at least one of entraining the water in an inert gas and operating the reactor column under a vacuum; and removing a product composition comprising the diphenolmethylene product at or proximate to the second end of the reactor column, wherein the removing of the water is sufficient such that the product composition is about 5 wt % or less water.

In another embodiment, a method of making a bisphenol, can comprise: feeding phenol at or proximate to the top end of a reactor column comprising a top end and a bottom end, the reactor column comprising a solid catalyst distributed in multiple locations between the top end and bottom end of the reactor column, wherein the reactor column has a holdup of the catalyst of about 20 vol % to about 60 vol %; feeding acetone to the reactor column at a first location that is at or proximate the top end and at one or more additional locations between the first location and the bottom end of the reactor column, wherein the reactor column is operated with a weight hourly space velocity of about 5 $h^{-1}$ to about 20 $h^{-1}$; contacting the phenol and the acetone compound in the reactor column in the presence of the catalyst sufficiently to condense the phenol and acetone to give bisphenol A (4,4'-(propane-2,2-diyl)diphenol) and water; removing at least some of the water from the reactor column by at least one of entraining the water in an inert gas injected at or proximate the bottom end of the reactor column and removed from the reactor column at or proximate to the top end of the reactor column, wherein a feed rate of the inert gas divided by the feed rate of the phenol and the acetone is about 0.01 L/kg to about 0.55 L/kg; and removing a product composition comprising the bisphenol A at or proximate to the bottom end of the reactor column, wherein the removing of the water is sufficient such that the product composition is about 2 wt % or less water, wherein about 8 wt % to about 35 wt % of the product composition is the bisphenol A, and in the product composition the concentration ratio of the bisphenol A divided by sum of the concentration of the bisphenol A and the concentration of all other side-products is about 70% to about 95%; wherein the method produces about 0.1 to about 2 kg of the bisphenol A per kg of the catalyst in the reactor column per hour (h) of performance of the method, and about 10 to about 1,000 kilogram (kg) of the bisphenol A per hour per cubic meter ($m^3$) of reactor column volume.

In an embodiment, an apparatus for making the bisphenol, can comprise: a reactor column comprising a first end and a second end, the reactor column comprising a solid catalyst distributed in multiple locations between the first end and the second end of the reactor column; a phenol inlet at or proximate to the first end of the reactor column configured for feeding of a substituted or unsubstituted phenol; a first oxomethylene inlet at or near the first end of the reactor column configured for feeding of an oxomethylene compound, wherein the oxomethylene compound has the structure $R^1$—C(O)—$R^2$, wherein $R^1$ and $R^2$ are each independently chosen from —H, halide, and a substituted or unsubstituted ($C_1$-$C_{10}$)hydrocarbyl, or $R^1$ and $R^2$ together form a substituted or unsubstituted ($C_1$-$C_{20}$)hydrocarbyl ring that comprises the —C(O)— of the oxomethylene compound; one or more additional oxomethylene inlets between the first oxomethlyene inlet and the second end of the reactor column configured for feeding of the oxomethylene compound, wherein the reactor column is configured such that the phenol and the oxomethylene compound contact one another in the reactor column in the presence of the catalyst sufficiently to condense the phenol and oxomethylene compound to give a diphenolmethylene product and water; and a product outlet at or proximate to the second end of the reactor column configured for removing a product composition comprising the diphenolmethylene product, wherein the reactor column is configured to remove the water by at entraining the water in an inert gas and operating under a vacuum, wherein the removing of the water is sufficient such that the product composition is about 5 wt % or less water.

BRIEF DESCRIPTION OF THE FIGURES

The drawings illustrate generally, by way of example, but not by way of limitation, various embodiments discussed in the present document.

DETAILED DESCRIPTION OF THE INVENTION

Figure 1C:
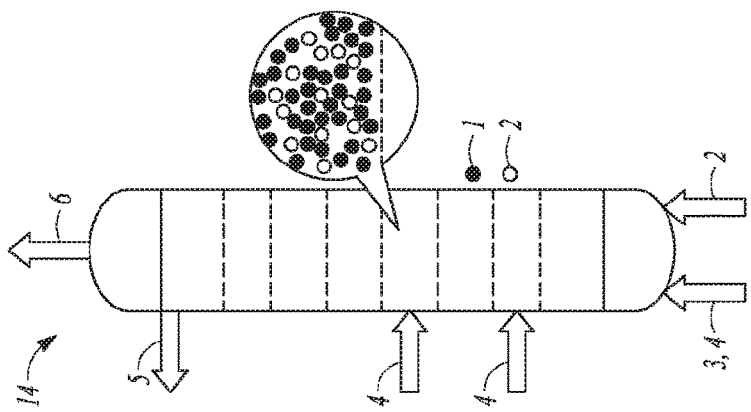
FIG. 1C illustrates a sectionalized slurry bubble column.

Reference will now be made in detail to certain embodiments of the disclosed subject matter, examples of which are illustrated in part in the accompanying drawings. While the disclosed subject matter will be described in conjunction with the enumerated claims, it will be understood that the exemplified subject matter is not intended to limit the claims to the disclosed subject matter.

Values expressed in a range format should be interpreted in a flexible manner to include not only the numerical values explicitly recited as the limits of the range, but also to include all the individual numerical values or sub-ranges encompassed within that range as if each numerical value and sub-range is explicitly recited. For example, a range of "about 0.1% to about 5%" or "about 0.1% to 5%" should be interpreted to include not just about 0.1% to about 5%, but also the individual values (e.g., 1%, 2%, 3%, and 4%) and the sub-ranges (e.g., 0.1% to 0.5%, 1.1% to 2.2%, 3.3% to 4.4%) within the indicated range. The statement "about X to Y" has the same meaning as "about X to about Y," unless indicated otherwise. Likewise, the statement "about X, Y, or about Z" has the same meaning as "about X, about Y, or about Z," unless indicated otherwise.

In this document, the terms "a," "an," or "the" are used to include one or more than one unless the context clearly dictates otherwise. The term "or" is used to refer to a nonexclusive "or" unless otherwise indicated. The statement "at least one of A and B" has the same meaning as "A, B, or A and B." In addition, it is to be understood that the phraseology or terminology employed herein, and not otherwise defined, is for the purpose of description only and not of limitation.

In the methods of manufacturing described herein, the steps can be carried out in any order, even concurrently, without departing from the principles of the invention, except when a temporal or operational sequence is explicitly recited. For example, a claimed step of doing X and a claimed step of doing Y can be conducted simultaneously within a single operation, and the resulting process will fall within the literal scope of the claimed process.

The term "about" as used herein can allow for a degree of variability in a value or range, for example, within 10% of a stated value or of a stated limit of a range.

The term "substantially" as used herein refers to a majority of, or mostly, as in at least about 50%, 60%, 70%, 80%, 90%, 95%, 96%, 97%, 98%, 99%, 99.5%, 99.9%, 99.99%, or at least about 99.999% or more.

The term "organic group" as used herein refers to any carbon-containing functional group. For example, an oxygen-containing group such as an alkoxy group, aryloxy group, aralkyloxy group, oxo(carbonyl) group; a carboxyl group including a carboxylic acid, carboxylate, and a carboxylate ester; a sulfur-containing group such as an alkyl and aryl sulfide group; and other heteroatom-containing groups. Non-limiting examples of organic groups include OR, OOR, OC(O)N(R)$_2$, CN, CF$_3$, OCF$_3$, R, C(O), methylenedioxy, ethylenedioxy, N(R)$_2$, SR, SOR, SO$_2$R, SO$_2$N(R)$_2$, SO$_3$R, C(O)R, C(O)C(O)R, C(O)CH$_2$C(O)R, C(S)R, C(O)OR, OC(O)R, C(O)N(R)$_2$, OC(O)N(R)$_2$, C(S)N(R)$_2$, (CH$_2$)$_{0-2}$N(R)C(O)R, (CH$_2$)$_{0-2}$N(R)N(R)$_2$, N(R)N(R)C(O)R, N(R)N(R)C(O)OR, N(R)N(R)CON(R)$_2$, N(R)SO$_2$R, N(R)SO$_2$N(R)$_2$, N(R)C(O)OR, N(R)C(O)R, N(R)C(S)R, N(R)C(O)N(R)$_2$, N(R)C(S)N(R)$_2$, N(COR)COR, N(OR)R, C(=NH)N(R)$_2$, C(O)N(OR)R, C(=NOR)R, and substituted or unsubstituted (C$_1$-C$_{100}$)hydrocarbyl, wherein R can be hydrogen (in examples that include other carbon atoms) or a carbon-based moiety, and wherein the carbon-based moiety can be substituted or unsubstituted.

The term "substituted" as used herein in conjunction with a molecule or an organic group as defined herein refers to the state in which one or more hydrogen atoms contained therein are replaced by one or more non-hydrogen atoms. The term "functional group" or "substituent" as used herein refers to a group that can be or is substituted onto a molecule or onto an organic group. Examples of substituents or functional groups include, but are not limited to, a halogen (e.g., F, Cl, Br, and I); an oxygen atom in groups such as hydroxy groups, alkoxy groups, aryloxy groups, aralkyloxy groups, oxo(carbonyl) groups, carboxyl groups including carboxylic acids, carboxylates, and carboxylate esters; a sulfur atom in groups such as thiol groups, alkyl and aryl sulfide groups, sulfoxide groups, sulfone groups, sulfonyl groups, and sulfonamide groups; a nitrogen atom in groups such as amines, hydroxyamines, nitriles, nitro groups, N-oxides, hydrazides, azides, and enamines; and other heteroatoms in various other groups. Non-limiting examples of substituents that can be bonded to a substituted carbon (or other) atom include F, Cl, Br, I, OR, OC(O)N(R)$_2$, CN, NO, NO$_2$, ONO$_2$, azido, CF$_3$, OCF$_3$, R, O(oxo), S(thiono), C(O), S(O), methylenedioxy, ethylenedioxy, N(R)$_2$, SR, SOR, SO$_2$R, SO$_2$N(R)$_2$, SO$_3$R, C(O)R, C(O)C(O)R, C(O)CH$_2$C(O)R, C(S)R, C(O)OR, OC(O)R, C(O)N(R)$_2$, OC(O)N(R)$_2$, C(S)N(R)$_2$, (CH$_2$)$_{0-2}$N(R)C(O)R, (CH$_2$)$_{0-2}$N(R)N(R)$_2$, N(R)N(R)C(O)R, N(R)N(R)C(O)OR, N(R)N(R)CON(R)$_2$, N(R)SO$_2$R, N(R)SO$_2$N(R)$_2$, N(R)C(O)OR, N(R)C(O)R, N(R)C(S)R, N(R)C(O)N(R)$_2$, N(R)C(S)N(R)$_2$, N(COR)COR, N(OR)R, C(=NH)N(R)$_2$, C(O)N(OR)R, and C(=NOR)R, wherein R can be hydrogen or a carbon-based moiety; for example, R can be hydrogen, (C$_1$-C$_{100}$)hydrocarbyl, alkyl, acyl, cycloalkyl, aryl, aralkyl, heterocyclyl, heteroaryl, or heteroarylalkyl; or wherein two R groups bonded to a nitrogen atom or to adjacent nitrogen atoms can together with the nitrogen atom or atoms form a heterocyclyl.

The term "alkyl" as used herein refers to straight chain and branched alkyl groups and cycloalkyl groups.

The term "alkenyl" as used herein refers to straight and branched chain and cyclic alkyl groups as defined herein, except that at least one double bond exists between two carbon atoms.

The term "acyl" as used herein refers to a group containing a carbonyl moiety wherein the group is bonded via the carbonyl carbon atom.

The term "cycloalkyl" as used herein refers to cyclic alkyl groups such as, but not limited to, cyclopropyl, cyclobutyl, cyclopentyl, cyclohexyl, cycloheptyl, and cyclooctyl groups. In some embodiments, the cycloalkyl group can have 3 to about 8-12 ring members, whereas in other embodiments the number of ring carbon atoms range from 3 to 4, 5, 6, or 7.

The term "aryl" as used herein refers to cyclic aromatic hydrocarbons that do not contain heteroatoms in the ring.

The term "heterocyclyl" as used herein refers to aromatic and non-aromatic ring compounds containing three or more ring members, of which one or more is a heteroatom such as, but not limited to, N, O, and S.

The term "heteroaryl" as used herein refers to aromatic ring compounds containing 5 or more ring members, of which, one or more is a heteroatom such as, but not limited to, N, O, and S; for instance, heteroaryl rings can have 5 to about 8-12 ring members. A heteroaryl group is a variety of a heterocyclyl group that possesses an aromatic electronic structure.

The terms "halo," "halogen," or "halide" group, as used herein, by themselves or as part of another substituent, mean, unless otherwise stated, a fluorine, chlorine, bromine, or iodine atom.

The term "hydrocarbon" as used herein refers to a functional group or molecule that includes carbon and hydrogen atoms. The term can also refer to a functional group or molecule that normally includes both carbon and hydrogen atoms but wherein all the hydrogen atoms are substituted with other functional groups.

The term "solvent" as used herein refers to a liquid that can dissolve a solid, liquid, or gas. Nonlimiting examples of solvents are silicones, organic compounds, water, alcohols, ionic liquids, and supercritical fluids.

As used herein, the term "polymer" refers to a molecule having at least one repeating unit and can include copolymers.

The present invention relates to an improved process for the production of bisphenols, such as bisphenol-A (also known as p,p-BPA/BPA). This improved process can give high conversion at high space velocities, which can result in a compact reactor design and fewer reactors for a given throughput. The design also enables simultaneous removal of water from the reaction mixture, which can eliminate the need for a downstream dehydration section. This can be achieved by the application of equipment that combine mass transfer with heterogeneous catalytic reaction such as sectionalized slurry bubble columns, catalytic structured packing columns, columns with alternating catalytic and non-catalytic sieve trays. The removal of water of reaction can be achieved by stripping with an inert gas or operation under vacuum.

Various embodiments provide a method of making a bisphenol. The method can include feeding a phenol at or proximate to the first end of a reactor column including a first end and a second end. The phenol can be substituted or unsubstituted. The method includes feeding an oxomethylene compound to the reactor column at a first location that is at or proximate the first end and at one or more additional locations between the first location and the second end of the reactor column. The location proximate the first end can be within about 30% of the total length of the column away from the first end, or within about 25%, 20, 15, 10, 5, 4, 3, 2, or within about 1% of the total length of the column away from the first end. The one or more additional locations can be any suitable locations along the length of the column between the first location and the second end of the column. In some embodiments, the one or more additional locations are evenly spaced from one another, while in other embodiments, the spacings between the additional locations can be different. In some embodiments, the additional locations can be within about 90% of the total length of the column away from the first end, or within about 80%, 70, 60, 50, 40, 30, or within about 20% of the total length of the column away from the first end. In some embodiments, the inlet for feeding the bisphenol and the inlet for feeding the oxomethylene compound at or proximate the first end of the column can be the same inlet, whereas in other embodiments the reactants can be fed to the column via two different inlets. There can be any suitable number of additional locations, such as 1, 2, 3, 4, 5, 6, 7, 8, 9, 10, 12, 14, 16, 18, 20, 25, 30, 35, 40, 45, or about 50 or more additional locations. At each acetone feed location, the acetone can be in a liquid phase, a vapor phase, or a combination thereof. The phenol fed to the column can be in a liquid phase, a vapor phase, or a combination thereof.

In various embodiments, the reactants and carrier fluids therefor (e.g., phenol, total oxomethylene compound fed in all feed locations, and any solvents, not including any inert gas) fed to the reactor column can be about 1 wt % to about 99 wt % phenol, about 5 wt % to about 98 wt %, 10 wt % to about 97 wt %, about 50 wt % to about 98 wt %, about 85 to about 98 wt % phenol, about 1 wt % or less, or about 2 wt %, 3, 4, 5, 6, 8, 10, 15, 20, 25, 30, 35, 40, 45, 50, 55, 60, 65, 70, 75, 80, 85, 86, 88, 90, 91, 92, 93, 94, 95, 96, 97, 98, or 99 wt % phenol or more. In various embodiments, the reactants fed to the reactor column and carrier fluids therefor can be about 0.01 wt % to about 50 wt % oxomethylene compound, about 0.01 wt % to about 25 wt %, 0.1 wt % to about 10 wt % oxomethylene compound, or about 0.01 wt % or less, about 0.05 wt %, 0.1, 0.5, 1, 2, 3, 4, 5, 6, 7, 8, 9, 10, 11, 12, 13, 14, 15, 16, 18, 20, 25, 30, 35, 40, 45, or about 50 wt % or more. Aside from the phenol and oxomethylene compound, the reactants fed can include any suitable proportion of any one or more carrier fluids, such as any suitable solvent.

In some embodiments, the first end of the reactor column is a top end and the second end of the reactor column is a bottom end, such that reactants are fed at or near the top of the column and the products are removed at or near the bottom. In other embodiments, the second end of the reactor column is a top end and the second end of the reactor column is a bottom end, such that the reactants are fed at or near the bottom of the column and the products are removed at or near the top.

The column can be any suitable column for performing the method, such that the phenol and oxomethylene compound can react as described herein to form the bisphenol product. In some embodiments, the reactor column is at least one of a bubble column, a trayed column, and a column with structured packing. The reactor column can be at least one of a sectionalized slurry bubble column, a column including catalytic structured packing, and a column including sieve trays including the catalyst and other sieve trays not including the catalyst (e.g., with the catalyst trays and non-catalyst trays alternating). The column can optionally include a reboiler, a condenser, one or more interstage coolers, and a combination thereof. The column can have any suitable height, such as about 1 m to about 200 m, or about 2 m to about 100 m, or about 1 m or less, or about 2, 4, 6, 8, 10, 12, 14, 16, 18, 20, 25, 50, 75, 100, 150, or about 200 m or more. The column can have any suitable diameter, such as about 1 cm to about 10 m, 1 cm to about 8 m, 1 cm to about 5 m, about 2 cm to about 3 m, about 3 cm to about 1 m, or about 1 cm or less, or about 2 cm, 4, 6, 8, 10, 12, 14, 16, 18, 20, 25, 50, 75, 1 m, 1.5, 2, 2.5, 3, 3.5, 4, 4.5, 5, 6, 7, 8, 9, or about 10 m or more.

The reactor column includes a solid catalyst distributed in multiple locations between the first end and the second end of the reactor column. The catalyst can be distributed in any suitable way within the column. The catalyst can be evenly distributed throughout the column, such as in the form of structures packing including the catalyst. The catalyst can be distributed on several different trays in the column.

The reactor column can include one catalyst or multiple catalysts. The catalyst can be any suitable catalyst for catalyzing the reaction of the phenol and the oxomethylene compound to form the biphenol. The catalyst can be an ion-exchange resin catalyst, such as a cation exchange resin. In some embodiments, the catalyst can be at least one selected from a metal foam supported acid catalyst, a covalently attached promoter catalyst, a chelating resin, a sulfonated polystyrene resin (e.g., crosslinked), a sulfonated divinyl benzene polystyrene copolymer (e.g., 1-8% crosslinked), a phenol-formaldehyde sulfonic acid resin, and a formaldehyde sulfonic acid resin.

The method includes contacting the phenol and the oxomethylene compound in the reactor column in the presence of the catalyst sufficiently to condense the phenol and oxomethylene compound to give a diphenolmethylene product and water. The method includes removing at least some of the water from the reactor column by at least one of entraining the water in an inert gas (e.g., in co-current or counter-current configuration) and operating the reactor column under a vacuum. The method includes removing a product composition including the diphenolmethylene product at or proximate to the second end of the reactor column. In some embodiments, the removing of the water in the reactor column can be sufficient such that the product composition is about 5 wt % or less water.

The method can include any suitable one or more subsequent steps, prior to the feeding of the phenol and the oxomethylene compound, or after the generation of the product composition by the reactor column. For example, the method can include at least one of subjecting the product composition to at least one of crystallization, distillation, desorption, and melt-crystallization. The method can include performing suitable steps to purify the product composition to provide the diphenolmethylene product at a purity of at least about 90 wt % without subjecting the product composition to dehydration, or a purity of about 50 wt % to about 99.999 wt %, or about 60 wt % to about 99 wt %, or about 50 wt % or less, or about 55 wt %, 60, 65, 70, 75, 80, 85, 86, 88, 90, 91, 92, 93, 94, 95, 96, 97, 98, 99, 99.9, 99.99, or about 99.999 wt % or higher purity.

The method can include feeding a promotor to the reactor column. The method can include the use of one promoter, or multiple promoters. The phenol and the oxomethylene can contact one another in the presence of the promoter. The promoter can be fed through the same inlet with the phenol, with the oxomethylene, or through a different inlet at or near the first end of the column. The promoter can be at least one of sulfur dichloride, sodium thiosulfate, hydrogen sulfide, iron sulfide, an alkanethiol (e.g., a $(C_1-C_{30})$alkanethiol), an arenethiol (e.g., a $(C_1-C_{30})$arenethiol), a thioglycolic acid, a mercaptoalkanesulfonic acid (e.g., a mercapto$(C_1-C_{30})$alkanesulfonic acid), an alkali alkyl xanthate (e.g., an alkali $(C_1-C_{30})$alkyl xanthate), 2-mercaptobenzothiazole, 2-mercaptoethylamine, a polymer-bound mercaptan promoter, and 3-mercaptopropionic acid. For example, the promoter is 3-mercaptopropionic acid.

Figure 1B:
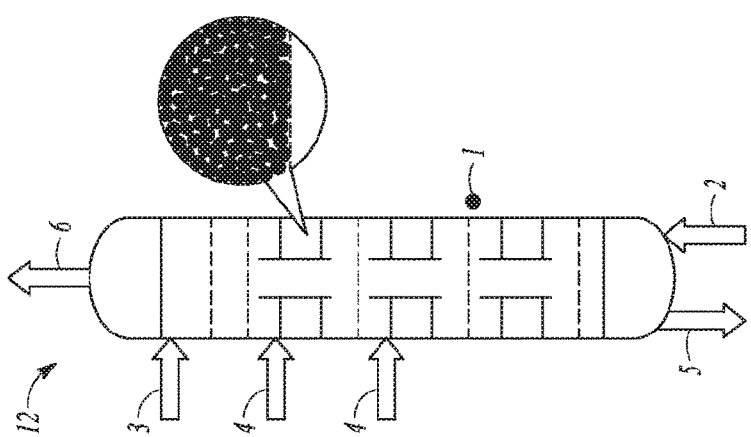
FIG. 1B illustrates a column with alternate reactive zones and separation zones.
Figure 1A:
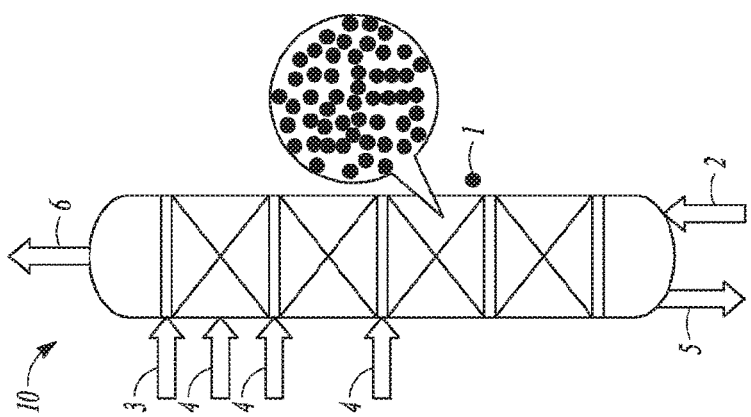
FIG. 1A illustrates a catalyst supported or immobilized on structured packing in a column.

FIG. 1A illustrates a catalyst 1 supported or immobilized on structured packing in a column 10. In some examples, the catalyst 1 can be ion-exchange resin (IER). The feed (phenol 3 and acetone 4) and nitrogen 2 are shown as counter-current. In some embodiments, catalyst loading per stage can be about 30% v/v. A gas-liquid disengagement zone is provided at the top. The structured packing is made of inert material and can have more than 70% voidage. Gases 6 exit the column, and BPA 5 is produced.

FIG. 1B illustrates a column 12 with alternate reactive zones (e.g., packed beds of IER catalyst 1) and separation zones (e.g., sieve trays or structured packing). The column has a chimney for gas traffic to reduce pressure drop. The feed (phenol 3 and acetone 4) and nitrogen 2 are shown as counter-current. The catalyst 1 is supported on a perforated tray, and can be immobilized by means of a mesh. The water of reaction can be removed in the separation zone (mass-transfer stages). Nitrogen 2 can be bypassed through a channel provided in reaction zone. A gas-liquid separation zone is provided at the top. Gases 6 exit the column, and BPA 5 is produced.

FIG. 1C illustrates a sectionalized slurry bubble column 14. The slurry bubble column is shown with co-current feed (phenol 3 and acetone 4) and nitrogen 2, but can alternatively operate in counter-current mode. A sieve tray along with mesh supports can avoid or reduce carryover of catalyst. A gas-liquid separation zone is provided at the top. Gases 6 exit the column, and BPA 5 is produced.

The method, or an apparatus for practicing the method, can include any suitable operating characteristics, such that the method can be performed as described herein.

The product composition removed from the column can have any suitable water content resulting from the removal of water in the reactor column. For example, the product composition can be about 5 wt % water or less, or about 2 wt % water or less, or about 0.01 wt % to about 5%, about 0.01 wt % to about 2 wt %, about 0.5 wt % to about 1.6 wt %, or about 0.01 wt % or less, 0.05 wt %, 0.1, 0.2, 0.3, 0.4, 0.5, 0.6, 0.7, 0.8, 0.9, 1, 1.1, 1.2, 1.3, 1.4, 1.5, 1.6, 1.7, 1.8, 1.9, 2, 2.2, 2.4, 2.6, 2.8, 3, 3.2, 3.4, 3.5, 4, 4.5, or about 5 wt % or more.

The product composition removed from the column can have any suitable proportion of the diphenolmethylene product (e.g., of the desired bisphenol, such as of bisphenol A). In some embodiments, about 5 wt % to about 50 wt % of the product composition is the diphenolmethylene product, about 8 wt % to about 35 wt %, or about 5 wt % or less, or about 6 wt %, 7, 8, 9, 10, 12, 14, 16, 18, 20, 22, 24, 26, 28, 30, 32, 34, 36, 38, 40, 42, 44, 46, 48, or about 50 wt % or more.

The method can selectively favor formation of the diphenolmethylene product. In some embodiments, the concentration of the diphenolmethylene product in the product composition (e.g., the concentration based on mass) divided by the sum of the concentration of the diphenolmethylene product and the concentration of all other side-products (e.g., the concentration based on mass) composition is about 50% to about 98%, about 70% to about 95%, or about 50% or less, or about 52%, 54, 56, 58, 60, 62, 64, 66, 68, 70, 72, 74, 76, 78, 80, 82, 84, 86, 88, 90, 92, 94, 96, or about 98% or more.

The reactor column can convert any suitable proportion of the total amount of oxomethylene compound fed to the column. In some embodiments, the conversion of the oxomethylene compound can be enhanced compared to other methods. In some embodiments, the conversion of the oxomethylene compound can be about 30 wt % to about 100 wt %, about 45 wt % to about 100 wt %, or about 30 wt % or less, or about 32 wt %, 34, 36, 38, 40, 42, 44, 45, 46, 48, 50, 52, 54, 56, 58, 60, 65, 70, 75, 80, 85, 86, 88, 90, 91, 92, 93, 94, 95, 96, 97, 98, 99, 99.9, 99.99, or about 99.999 wt % or more.

The method can have enhanced productivity compared to other methods. The method can have any level of productivity. In some embodiments, the reactor column can produce about 0.05 to about 5 kg of the diphenolmethylene product per kg of the catalyst in the reactor column per hour of performance of the method, or about 0.1 to about 2 kg, about 0.1 to about 0.5, or about 0.05 or less, or about 0.1, 0.2, 0.4, 0.6, 0.8, 1, 1.1, 1.2, 1.3, 1.4, 1.5, 1.6, 1.7, 1.8, 1.9, 2, 2.5, 3, 3.5, 4, 4.5, or about 5 kg or more of the diphenolmethylene product per kg of the catalyst in the reactor column per hour of performance of the method. The reactor column can produce about 1 to about 50,000 kg of the diphenolmethylene product per hour per m$^3$ of reactor column volume, about 5 to about 5,000, about 10 to about 1,000, about 30 to about 600, or about 1 or less, or about 2, 3, 4, 5, 6, 8, 10, 12, 14, 16, 18, 20, 25, 30, 35, 40, 45, 50, 60, 70, 80, 90, 100, 110, 120, 130, 140, 150, 160, 170, 180, 190, 200, 250, 500, 750, 1,000, 1,500, 2,000, 2,500, 5,000, 10,000, 15,000, 20,000, 25,000, 30,000, 40,000, or about 50,000 kg or more of the diphenolmethylene product per hour per m$^3$ of reactor column volume.

For embodiments including injection of an inert gas into the column, the inert gas can be injected into any suitable locations, such as at or proximate to a bottom end of the reactor column. The inert gas can be removed from the column at any suitable location, such as at or proximate to a top end of the reactor column. The inert gas can have a co-current or counter-current flow with the phenol and oxomethylene and corresponding products generated. The feed rate of the inert gas can be any suitable feed rate. In some embodiments, the feed rate of the inert gas divided by a feed rate of the phenol and the oxomethylene compound can be about 0.001 liters per kilogram (L/kg) to about 3 L/kg, about 0.01 L/kg to about 1 L/kg, about 0.01 L/kg to about 0.6 L/kg, or about 0.001 L/kg or less, or about 0.005 L/kg, 0.01, 0.05, 0.1, 0.5, 1, 1.5, 2, 2.5, or about 3 L/kg or more. The inert gas can have any suitable velocity from one end of the reactor to the other end (e.g., from the bottom end to the top end), such as about 0.01 cm/sec to about 30 cm/sec, about 0.1 cm/sec to about 10 cm/sec, about 8 cm/sec to about 30 cm/sec, about 10 cm/sec to about 30 cm/sec, about 15 cm/sec to about 30 cm/sec, or about 0.01 cm/sec or less, or about 0.05 cm/sec, 0.1, 0.5, 1, 2, 3, 4, 5, 6, 8, 10, 12, 14, 16, 18, 20, 22, 24, 26, 28, or about 30 cm/sec or more.

For embodiments including operation of the column under a vacuum, the vacuum can be any suitable pressure that is less than atmospheric pressure (e.g., less than about 101 kiloPascals (kPa)). In some embodiments, the vacuum can be about 0.000, 1 kPa to about 100 kPa, or about 0.000, 1 kPa or less, or about 0.001 kPa, 0.01, 0.1, 0.5, 1, 2, 3, 4, 5, 6, 8, 10, 12, 14, 16, 18, 20, 25, 50, 75, or about 100 kPa or more.

The reactor column can have any suitable holdup of the catalyst, e.g., the amount of the column occupied by the catalyst. In some embodiments, the reactor column can have a holdup of catalyst of about 10 vol % to about 80 vol %, about 20 vol % to about 60 vol %, about 25 vol % to about 55 vol %, or about 10 vol % or less, or about 12 vol %, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, or about 80 vol % or more.

The method can include operating the reactor column at any suitable space velocity. For example, the method can include operating the reactor column at a weight hourly space velocity of about 0.1 h$^{-1}$ to about 30 h$^{-1}$, about 0.5 h$^{-1}$ to about 5 h$^{-1}$, about 5 h$^{-1}$ to about 20 h$^{-1}$, or about 0.1 h$^{-1}$ or less, or about 0.2, 0.4, 0.5, 0.6, 0.8, 1, 1.5, 2, 2.5, 3, 3.5, 4, 4.5, 5, 6, 7, 8, 9, 10, 11, 12, 13, 14, 15, 16, 17, 18, 19, 20, 22, 24, 26, 28, or about 30 h$^{-1}$ or more.

The reactor column can be operated with any suitable temperature profile. In various embodiments, the reactor column can have an isothermal temperature profile, an adiabatic temperature profile, or a higher temperature at the first end and a lower temperature at the second end.

In some embodiments, the phenol is an unsubstituted hydroxybenzene, the oxomethylene compound is acetone, and the product is bisphenol A (4,4'-(propane-2,2-diyl)diphenol). In the product composition the ratio of the 4,4'-(propane-2,2-diyl)diphenol to 2,4'-(propane-2,2-diyl)diphenol is about 5 to about 30, about 8 to about 15, or about 5 or less, or about 6, 7, 8, 9, 10, 11, 12, 13, 14, 15, 16, 18, 20, 22, 24, 26, 28, or about 30 or more.

The method includes contacting the phenol and the oxomethylene compound in the reactor column in the presence of the catalyst sufficiently to condense the phenol and oxomethylene compound to give a diphenolmethylene product and water. Two molecules of the phenol can combine with one molecule of the oxomethylene to give one molecule of product and one molecule of water. In some embodiments, the method includes using feeding one type of phenol compound. In some embodiments, the method includes feeding two or more phenol compounds to the reactor column, each having different chemical structures. In some embodiments, the method includes feeding one type of oxomethylene compound. In some embodiments, the method includes feeding two or more oxomethylene compounds to the reactor column, each having different chemical structures.

The phenol can be substituted or unsubstituted. In some embodiments, the phenol is substituted with 1, 2, 3, or 4 groups independently selected from ($C_1$-$C_{20}$)hydrocarbyl and halo. The phenol can be substituted with 1, 2, 3, or 4 ($C_1$-$C_5$)alkyl groups. The phenol can be chosen from phenol, cresol, 2-isopropylphenol, and 2-phenylphenol. The phenol can be an unsubstituted hydroxybenzene.

The oxomethylene compound has the structure $R^1$—C(O)—$R^2$. The variables $R^1$ and $R^2$ can be each independently chosen from —H, halide, and a substituted or unsubstituted ($C_1$-$C_{10}$) hydrocarbyl. Alternatively, the variables $R^1$ and $R^2$ together can form a substituted or unsubstituted ($C_1$-$C_{20}$) hydrocarbyl ring (e.g., $C_5$, $C_6$, $C_7$, or $C_8$) that includes the —C(O)— of the oxomethylene compound. The variables $R^1$ and $R^2$ can be each independently chosen from —H and ($C_1$-$C_{10}$)alkyl. In some embodiments, the oxomethylene compound can be chosen from acetone, acetophenone, hexafluoroacetone, butanone, benzophenone, acetaldehyde, formaldehyde, substituted or unsubstituted cyclohexanone, and 3,3,5-trimethylcyclohexanone. The oxomethylene compound can be acetone.

The diphenolmethylene formed by condensation of the phenol and the oxomethylene can be any suitable diphenolmethylene. For example, the diphenolmethylene can be at least one chosen from bisphenol A (2,2-bis(4-hydroxyphenyl)propane), bisphenol AP (1,1-bis(4-hydroxy phenyl)-1-phenyl-ethane), bisphenol AF (2,2-bis(4-hydroxyphenyl) hexafluoropropane), bisphenol B (2,2-bis(4-hydroxyphenyl) butane), bisphenol BP (bis-(4-hydroxyphenyl) diphenylmethane), bisphenol C (2,2-bis(3-methyl-4-hydroxyphenyl)propane), bisphenol E (1,1-Bis(4-hydroxyphenyl) ethane), bisphenol F (bis(4-hydroxydiphenyl)methane), bisphenol G (2,2-bis(4-hydroxy-3-isopropyl-phenyl)propane), bisphenol PH (5,5'-(1-methylethyliden)-bis[1,1'-(bisphenyl)-2-ol]propane), bisphenol TMC (1,1-bis(4-hydroyphenyl)-3,3,5-trimethyl-cyclohexane), and bisphenol Z (1,1-bis(4-hydroxyphenyl)-cyclohexane). In some embodiments, the diphenolmethylene is bisphenol A (4,4'-(propane-2,2-diyl)diphenol).

In various embodiments, the present invention provides an apparatus. The apparatus can be any suitable apparatus that can be used to perform an embodiment of the method described herein. The apparatus can include a reactor column including a first end and a second end. The reactor column can include a solid catalyst distributed in multiple locations between the first end and the second end of the reactor column. The apparatus can include a phenol inlet at or proximate to the first end of the reactor column configured for feeding of a substituted or unsubstituted phenol, such as an unsubstituted hydroxybenzene. The apparatus can include a first oxomethylene inlet at or near the first end of the reactor column configured for feeding of an oxomethylene compound having the structure $R^1$—C(O)—$R^2$. The variables $R^1$ and $R^2$ can be each independently chosen from —H, halide, and a substituted or unsubstituted ($C_1$-$C_{10}$) hydrocarbyl, or $R^1$ and $R^2$ together form a substituted or unsubstituted ($C_1$-$C_{20}$)hydrocarbyl ring that includes the —C(O)— of the oxomethylene compound. In some embodiments, the oxomethylene compound is acetone. The apparatus can include one or more additional oxomethylene inlets between the first oxomethlyene inlet and the second end of the reactor column configured for feeding of the oxomethylene compound. The reactor column can be configured such that the phenol and the oxomethylene compound can contact one another in the reactor column in the presence of the catalyst sufficiently to condense the phenol and oxomethylene compound to give a diphenolmethylene product and water. In some embodiments, the diphenolmethylene product can be bisphenol A. The apparatus can include a product outlet at or proximate to the second end of the reactor column configured for removing a product composition including the diphenolmethylene product. The reactor column can be configured to remove the water by at least one of entraining the water in an inert gas and operating under a vacuum, wherein the removing of the water is sufficient such that the product composition is about 5 wt % or less water.

EXAMPLES

Various embodiments of the present invention can be better understood by reference to the following Examples which are offered by way of illustration. The present invention is not limited to the Examples given herein.

Example 1. Bisphenol A (BPA) Reactive Stripper

A modified lab Kühni™ extraction column, resembling a sectionalized bubble column design, was used for this Example. It had five sections, out of which the top two sections were modified by removing impellers and horizontal baffles to achieve gas-liquid separation and removal of product, while the bottom three sections were used primarily for the reaction. Each section was separated by providing a SS316 screen of size 100 mesh, to support and prevent carryover of the ion-exchange resin (IER) catalyst. All the feed and product lines were heat traced and insulated to avoid freezing of reactants. The jacket of the Kühni™ extraction column was divided in two parts to help achieve the temperature profile inside the column. The bottom section of the column had a first utility supply and the top four sections had a second utility supply. Hot nitrogen was supplied at the column bottom through a non-return valve and a glass sintered plate to ensure distribution of gas in small bubbles. Exit gas from top of the column was cooled to condense entrained water, phenol and acetone. IER catalyst used in experiments was from Lanxess™ 2% Cl, K1131S. Experiments were performed using two different quantities of pre-dried IER catalyst 60 g and 120 g; the catalyst was divided in three equal parts and charged in three reaction sections. Reagents used were of GR grade from Merck™. Positive displacement piston pumps from FMI™ were used to pump the feed and intermediate acetone. Liquid flow rates were inferred from the pump calibration curve. Nitrogen flow was controlled by means of an analog thermal mass flow controller from MKS™. Agitation speed was measured using a tachometer.

Figure 2:
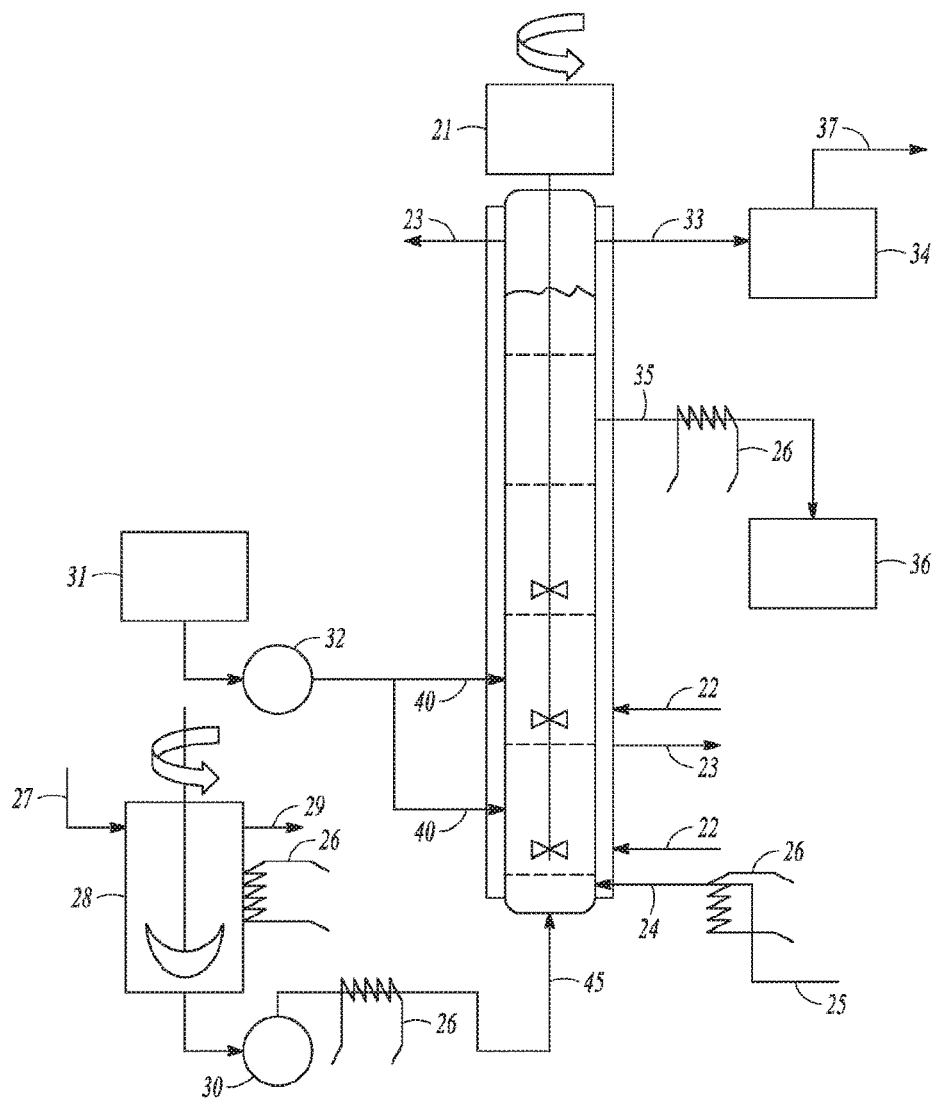
FIG. 2 illustrates a process flow including a reactor column.

FIG. 2 shows a process flow diagram of the BPA reactive stripping experimental setup used for rungs 4, 13, and 14. The Kühni™ extraction column 20 had an internal diameter of 32 mm. The column had a total number of 5 sections, with 2 gas-liquid separation sections and 3 reacting sections. The column had a stator/horizontal baffle opening diameter of 12 mm. The column had 10 compartments formed by stator per section. The column had a compartment height of 22 mm. The column was used in an upflow mode of operation, with co-current feed and nitrogen flow. The column had 3 acetone feeds, one with the phenol feed, one at the middle of the bottom reactive section, and one at the center of the middle reactive section. The sparge point for the inert gas (nitrogen, 25) was at the bottom of the column. The catalyst was (2% Cl, K1131S Lanxess), particle size 600 micron. The catalyst volumetric holdup of the reactor column (e.g., the percent of the total reactor volume that was occupied by catalyst) was calculated at about 50%. The targeted total acetone concentration for all feeds to the column was 5 wt %. Aside from the bottom stage feed, acetone was fed in two additional streams: midway on bottom stage (1.5-2 wt %) and midway on the middle stage (1-1.5 wt %). The column 20 had a motor 21 for turning the rotors. Hot water streams 22 and 23 flowed through the column to regulate temperature. Acetone, phenol, 3-MPA flowed from storage vessel 28, having a nitrogen atmosphere via nitrogen feed 27 and vent 29, through pump 30 and into the column 20 via feed 45. Acetone flowed from storage vessel 31 through pump 32 and into the column 20 via feeds 40. Nitrogen gas 25 was sparged into the column via feed 24. The product stream exited the column 20 at line 35 and was stored in tank 36. The column included a nitrogen vent 33 to vent nitrogen 37 via cold trap 34. For runs 1, 7, and 8, a similar experimental setup was used, but with a packed-bed column, with no sparging of inert gas.

Table 1 gives the results of the experiment. Runs 1, 7, and 8 in Table 1 used a plug flow reactor arrangement with no sparged gas (comparative examples), while runs 4, 13, and 14 used a reactor column with co-current sparged gas and reactants. The BPA productivity with the plug flow arrangement was lesser than stripping reactor arrangement. Bisphenol A is 4,4'-(propane-2,2-diyl)diphenol. WHSV is weight hourly space velocity. 3MPA is 3-mercaptopropionic acid. Dimer is a product formed by combination of two 2(4-hydroxyphenyl)propan-2-ylium intermediates. Chroman is 2,4,4-trimethyl-2-(4-hydroxyphenyl)chroman and 4-(2,2,4-trimethylchroman-4-yl)phenol. BPX-1 and BPX-2 are trimmers formed by combination of three 2(4-hydroxyphenyl)propan-2-ylium intermediates, with BPX-1 being 4,4'-((4-hydroxy-1,3-phenylene)bis(propane-2,2-diyl))diphenol and BPX-2 being 4-(2-(4-(4-hydroxyphenyl)-2,2,4-trimethylchroman-6-yl)propan-2-yl)phenol. SBI is spiro(bis)indane cyclic dimer. DMX is 4,4'-((4-hydroxy-1,3-phenylene)bis(propane-2,2-diyl))diphenol. Heavies are the remainder of the impurities. pp/op is the ratio of 4,4'-(propane-2,2-diyl)diphenol to 2,4'-(propane-2,2-diyl)diphenol.

acetone, and promotor feed 53, with additional acetone feeds 61, and catalyst 62. The reactor column 50 includes drive motor 51, gearbox 52, vessel walls 53, shaft 54, stators 55, and rotors 56. The reactor column 50 is sparged with inert gas 64. Factors that can affect performance include feed flowrate/WHSV 65, reaction temperature or profile 66, agitation 67, nitrogen:feed ratio 68, overall acetone concentration 69, number of acetone feed splits 70, and promoter concentration 71.

In this Example, the factors of feed flowrate, reaction temperature, agitation, and nitrogen:feed ratio were studied, while the remaining factors were held constant. The same Experimental setup was used as described in Example 1 (run 1 was packed bed with no inert gas sparging, runs 2-6 were co-current sparged gas and reactants as shown in FIG. 2).

The material balance for acetone was unable to close because of acetone losses in the exit gas due to partial

TABLE 1

Reactive column in co-current or counter-current mode.

| Set parameter | Unit | Sr. no. 1 Base case (packed bed) | Sr. no. 7 Base case (packed bed) | Sr. no. 8 Base case (packed bed) | 4 | 13 | 14 |
|---|---|---|---|---|---|---|---|
| Agitator speed | RPM | 10 | 10 | 0 | 100-200 | 0 | 0 |
| Catalyst quantity | g | 60 | 120 | 120 | 60 | 120 | 120 |
| Feed flow | g/hr | 60 | 120 | 120 | 300 | 240 | 240 |
| WHSV | hr$^{-1}$ | 1 | 1 | 1 | 5 | 2 | 2 |
| Nitrogen flow | mL/min | 0 | 0 | 0 | 64 | 950 | 2200 |
| Ratio of Nitrogen to liquid flow | L/g | 0 | 0 | 0 | 0.0128 | 0.2375 | 0.55 |
| Jacket temperature, Bottom stage | ° C. | 65 | 65 | 65 | 82 | 70 | 85 |
| Jacket temperature, Middle and top stage | ° C. | 82 | 80 | 80 | 72 | 70 | 85 |
| Overall Acetone concentration | wt % | 5 | 5 | 5 | 5 | 5 | 5 |
| FEED ANALYSIS | | | | | | | |
| Acetone, bottom stage inlet | % w/w | 3.6 | 5.268 | 3.908 | | 2.39 | 2.39 |
| Promoter, 3 MPA | SH, ppm | 1300 | 1300 | 1300 | 1300 | 1300 | 1300 |
| Phenol | % w/w | 96.4 | 94.7 | 96.1 | | 97.6 | 97.6 |
| PRODUCT ANALYSIS | | | | | | | |
| Acetone | % w/w | | 0.670 | 0.593 | <0.5 | 0.830 | 0.440 |
| Phenol | % w/w | 83.72 | 80.92 | 83.86 | 90.42 | 82.93 | 81.78 |
| Water | % w/w | 1.52 | 1.452 | 1.389 | 1.1 | 0.604 | 0.603 |
| | | | 1.468 | 1.41 | | 0.555 | 0.580 |
| p,p-BPA | % w/w | 13.543 | 16.86 | 13.28 | 8.791 | 14.35 | 12.54 |
| o,p-BPA | % w/w | 0.927 | 1.126 | 1.555 | 0.619 | 1.263 | 1.539 |
| Dimer | % w/w | 0.060 | 0.028 | 0.041 | 0.058 | 0.028 | 0.039 |
| | | | 0.022 | 0.067 | | 0.112 | 1.537 |
| | | | 0.040 | 0.046 | | 0.024 | 0.072 |
| Chroman | % w/w | 0.060 | 0.028 | 0.078 | 0.034 | 0.062 | 0.039 |
| | | | 0.071 | 0.105 | | 0.096 | 0.250 |
| BPX-1 | % w/w | 0.136 | 0.174 | 0.214 | 0.055 | 0.205 | 0.288 |
| BPX-2 | % w/w | 0.006 | 0.015 | 0.029 | 0.006 | 0.031 | 0.054 |
| SBI | % w/w | 0.000 | 0.001 | 0.028 | 0.001 | 0.012 | 1.114 |
| DMX | % w/w | 0.000 | 0.000 | 0.000 | 0.000 | 0.001 | 0.030 |
| Heavies | % w/w | 0.025 | 0.040 | 0.091 | 0.011 | 0.050 | 0.270 |
| pp/op | | 14.608 | 14.982 | 8.547 | 14.212 | 11.366 | 8.151 |
| Productivity | kg BPA/kg catalyst · hr | 0.1354 | 0.1686 | 0.1328 | 0.4395 | 0.287 | 0.2508 |
| P,p-BPA Selectivity | % | 91.778 | 91.61 | 85.49 | 91.811 | 88.40 | 70.56 |
| Acetone consumed | % w/w | 3.780 | 4.72 | 4.02 | 2.456 | 4.20 | 5.18 |
| Acetone conversion | % w/w | 105.030 | 94.47 | 102.90 | 49.110 | 84.01 | 103.57 |

Example 2. Performance of Bisphenol A Reaction Column

Figure 3:
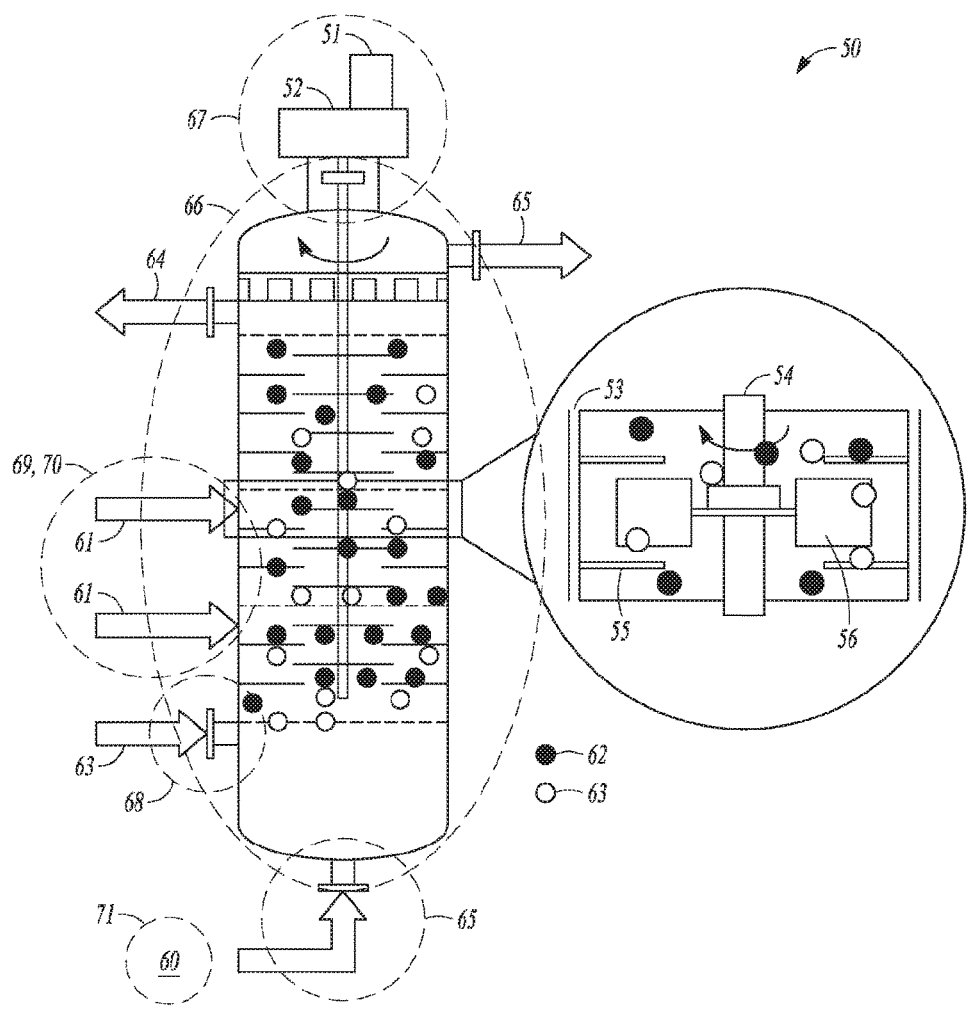
FIG. 3 illustrates factors that can affect the performance of a bisphenol A reactor column.

Various factors can affect the performance of a BPA reactor column 50 illustrated in FIG. 3, having phenol, condensation. Various characteristics were calculated as follows, with the same conventions being followed in Example 1. The % acetone conversion was calculated as 100*(% acetone in feed−% acetone consumed)/% acetone in feed. The % p,p-BPA selectivity was calculated as 100*(% p,p-BPA in product–% p,p-BPA in feed)/(% p,p-BPA and impurities in product–% p,p-BPA and impurities in feed). The % impurities was calculated as o,p-BPA+Dimer+Chroman+BPXI+BPXII+SBI+DMX+Heavies. The % acetone consumed was calculated based on product composition.

Example 2.1

This Example used 60 g of IER catalyst, with an overall acetone concentration of 5% w/w (distributed as: reactor feed 2% w/w, middle stage 2% w/w and middle stage 1% w/w). The feed was fresh phenol, acetone, and 3MPA. The results of the experiments are given in Table 2.

closed. However, it can be observed that acetone consumed (inferred from product composition) in experiment numbers 5 and 6 is comparable to the base case experiment.

Experiments confirm that catalyst suspension by agitation allows operation at WHSV>1 hr$^{-1}$ by overcoming hydraulic limitations. It was seen that catalyst suspension was non-uniform and liquid mixing was not intense, most likely due to inadequate nitrogen flow.

Example 2.2

This Example was performed with 120 g of IER catalyst, with an overall acetone concentration of 5% w/w (distrib-

TABLE 2

BPA reactive stripping results - low superficial gas velocity.

| | | Sr. no. | | | | | |
|---|---|---|---|---|---|---|---|
| Set parameter | Unit | 1 Base case (packed bed) | 2 | 3 WHSV effect | 4 | 5 | 6 Low temperature |
| Agitator speed | RPM | 10 | 100-200 | 100-200 | 100-200 | 100-200 | 100-200 |
| WHSV (feed flow) | hr$^{-1}$ (g/hr) | 1 (60) | 1 (60) | 2 (120) | 5 (300) | 1 (60) | 2 (120) |
| Nitrogen/liquid ratio (Nitrogen flow) | L/g (Nitrogen flow, mL/min) | 0 | 0.054 (54) | 0.032 (64) | 0.0128 (64) | 0.08 (80) | 0.05 (100) |
| Jacket temperature, Bottom stage | ° C. | 65 | 82 | 82 | 82 | 72 | 72 |
| Jacket temperature, Middle and top stage | ° C. | 82 | 72 | 72 | 72 | 67 | 67 |
| Overall Acetone concentration | wt % | 5 | 5 | 5 | 5 | 5 | 5 |
| Time of sampling | hrs | 40 | 39 | 18 | 7 | 44 | 20 |
| FEED ANALYSIS | | | | | | | |
| Acetone, bottom stage inlet | % w/w | 3.6 | | | | 1.6 | |
| Promoter, 3 MPA | SH, ppmw | 1300 | 1300 | 1300 | 1300 | 1300 | 1300 |
| Phenol | % w/w | 96.4 | | | | 98.4 | |
| PRODUCT ANALYSIS | | | | | | | |
| Acetone | % w/w | | <0.5 | | | | |
| Phenol | % w/w | 83.72 | 89.588 | 89.18 | 90.42 | 82.52 | 84.620 |
| Water | % w/w | 1.52 | | 1.1299 | | 1.1249 | 0.947 |
| p,p-BPA | % w/w | 13.543 | 9.343 | 8.819 | 8.791 | 15.028 | 13.440 |
| o,p-BPA | % w/w | 0.927 | 0.815 | 0.695 | 0.619 | 1.006 | 0.777 |
| Dimer | % w/w | 0.060 | 0.094 | 0.063 | 0.058 | 0.068 | 0.049 |
| Chroman | % w/w | 0.060 | 0.046 | 0.033 | 0.034 | 0.064 | 0.043 |
| BPX-1 | % w/w | 0.136 | 0.086 | 0.063 | 0.055 | 0.157 | 0.106 |
| BPX-2 | % w/w | 0.006 | 0.007 | 0.005 | 0.006 | 0.008 | 0.004 |
| SBI | % w/w | 0.000 | 0.001 | 0.000 | 0.001 | 0.000 | 0.000 |
| DMX | % w/w | 0.000 | 0.000 | 0.000 | 0.000 | 0.000 | 0.000 |
| Heavies | % w/w | 0.025 | 0.019 | 0.010 | 0.011 | 0.020 | 0.014 |
| pp/op | | 14.608 | 11.465 | 12.698 | 14.212 | 14.942 | 17.305 |
| Productivity | kg BPA/kg catalyst · hr | 0.1354 | 0.09343 | 0.1763 | 0.4395 | 0.15 | 0.268 |
| Selectivity | % | 91.778 | 89.740 | 91.039 | 91.811 | 91.915 | 93.122 |
| Acetone consumed | % w/w | 3.780 | 2.670 | 2.480 | 2.456 | 4.192 | 3.694 |
| Acetone conversion | % | 105.030 | 53.550 | 49.700 | 49.110 | 83.84 | 73.88 |

This Example was performed at low nitrogen:liquid feed ratio and with agitation. The base case experiments were performed at very low RPM, to avoid channeling. It can be observed from experiment numbers 2 to 6 that p,p-BPA selectivity is not affected by the increase of feed flowrate. The experiments performed at lower temperature show improved selectivity. The lowest water concentration achieved by stripping is 0.947% w/w in experiment number 6.

Effect of water removal on improving acetone conversion were not observed by comparing base case vs. stripping experiments because the acetone mass balance was not uted as follows: reactor feed 2% w/w, middle stage 1.5% w/w and middle stage 1.5% w/w). The feed was fresh phenol, acetone, and 3MPA. Highest superficial gas velocity of operation was 4.55 cm/sec. The results of the experiments are given in Table 3. LD-1 is 4,4'-(4-methylpent-2-ene-2,4-diyl)diphenol or 4,4'-(4-methylpent-1-ene-2,4-diyl)diphenol. CD-1 is 3-(4-hydroxyphenyl)-1,1,3-trimethyl-2,3-dihydro-1H-inden-5-ol. CD-2 is 1-(4-hydroxyphenyl)-1,3,3-trimethyl-2,3-dihydro-1H-inden-5-431). Chroman 1 is 4-(2,2,4-trimethylchroman-4-yl)phenol. Chroman 1.5 is 4-(2,4,4-trimethylchroman-2-yl)phenol.

TABLE 3

BPA reactive stripping results - high superficial gas velocity.

| Set parameter | Unit | Sr. no. 7 Base case (packed bed) | 8 | 9 | 10 |
|---|---|---|---|---|---|
| Agitation | RPM | 10 | 0 | 0 | 0 |
| WHSV (feed flow) | hr−1 (g/hr) | 1 (120) | 1 (120) | 1 (120) | 1 (120) |
| Nitrogen/Liquid ratio (Nitrogen flow) | L/g (Nitrogen flow, mL/min) | 0 | 0 | 0.2375 (475) | 0.55 (1100) |
| Jacket Temperature Bottom stage | ° C. | 65 | 65 | 85 | 70 |
| Jacket Temperature Middle and top stage | ° C. | 80 | 80 | 85 | 70 |
| Overall Acetone concentration | wt % | 5 | 5 | 5 | 5 |
| Nitrogen superficial velocity | cm/sec | 0 | 0 | 0.98 | 2.27 |
| FEED ANALYSIS | | | | | |
| Acetone, bottom stage inlet | % w/w | 5.268 | 3.908 | 2.12 | 2.22 2.408 |
| Promoter, 3 MPA | SH, ppm | 1300 | 1300 | 1300 | 1300 |
| PRODUCT ANALYSIS | | | | | |
| Acetone | % w/w | 0.670 | 0.593 | 0.506 | 0.629 |
| Water | % w/w | 1.452 1.468 | 1.389 1.41 | 0.385 0.450 | 0.440 |
| Phenol | % w/w | 80.92 | 83.86 | 86.48 | 84.97 |
| p,p-BPA | % w/w | 16.86 | 13.28 | 10.52 | 12.39 |
| o,p-BPA | % w/w | 1.126 | 1.555 | 1.233 | 1.103 |
| LD-1 | % w/w | 0.028 | 0.041 | 0.033 | 0.025 |
| CD-1 | % w/w | 0.022 | 0.067 | 0.658 | 0.157 |
| CD-2 | % w/w | 0.040 | 0.046 | 0.020 | 0.014 |
| Chroman 1 | % w/w | 0.028 | 0.078 | 0.007 | 0.003 |
| Chroman 1.5 | % w/w | 0.071 | 0.105 | 0.099 | 0.062 |
| BPX-1 | % w/w | 0.174 | 0.214 | 0.145 | 0.139 |
| BPX-2 | % w/w | 0.015 | 0.029 | 0.021 | 0.010 |
| SBI | % w/w | 0.001 | 0.028 | 0.132 | 0.009 |
| DMX | % w/w | 0.000 | 0.000 | 0.021 | 0.000 |
| Heavies | % w/w | 0.040 | 0.091 | 0.113 | 0.037 |
| pp/op, Product | | 14.982 | 8.547 | 8.541 | 11.240 |
| Productivity | kg BPA/kg catalyst · hr | 0.1686 | 0.1328 | 0.1052 | 0.1239 |
| pp-BPA Selectivity | % | 91.61 | 85.49 | 80.93 | 88.82 |
| Acetone consumed | % w/w | 4.72 | 4.02 | 3.49 | 3.60 |
| Acetone conversion | % | 94.47 | 102.90 | 69.66 | 72.07 |
| Selectivity overall | % | 97.73 | 95.50 | 90.41 | 96.73 |

| Set parameter | Sr. no. 11 | 12 | 13 | 14 |
|---|---|---|---|---|
| Agitation | | 0 | 0 | 0 |
| WHSV (feed flow) | 2 (240) | 1 (120) | 2 (240) | 2 (240) |
| Nitrogen/Liquid ratio (Nitrogen flow) | 0.55 (2200) | 0.55 (1100) | 0.2375 (950) | 0.55 (2200) |
| Jacket Temperature Bottom stage | 85 | 70 | 70 | 85 |
| Jacket Temperature Middle and top stage | 85 | 70 | 70 | 85 |
| Overall Acetone concentration | 5 | 5 | 5 | 5 |
| Nitrogen superficial velocity | 4.55 | 2.27 | 1.96 | 4.55 |
| FEED ANALYSIS | | | | |
| Acetone, bottom stage inlet | 2.212 | 1.95 | 2.39 | 2.39 |
| Promoter, 3 MPA | 1300 | 1300 | 1300 | 1300 |
| PRODUCT ANALYSIS | | | | |
| Acetone | 0.443 | 0.583 0.553 | 0.830 | 0.440 |
| Water | 0.237 0.235 | 0.779 0.782 | 0.604 0.555 | 0.603 0.580 |
| Phenol | 87.79 | 88.23 | 82.93 | 81.78 |
| p,p-BPA | 9.31 | 10.22 | 14.35 | 12.54 |
| o,p-BPA | 1.122 | 1.010 | 1.263 | 1.539 |

TABLE 3-continued

BPA reactive stripping results - high superficial gas velocity.

| | | | | |
|---|---|---|---|---|
| LD-1 | 0.030 | 0.023 | 0.028 | 0.039 |
| CD-1 | 0.696 | 0.203 | 0.112 | 1.537 |
| CD-2 | 0.023 | 0.014 | 0.024 | 0.072 |
| Chroman 1 | 0.007 | 0.006 | 0.062 | 0.039 |
| Chroman 1.5 | 0.091 | 0.063 | 0.096 | 0.250 |
| BPX-1 | 0.128 | 0.138 | 0.205 | 0.288 |
| BPX-2 | 0.021 | 0.016 | 0.031 | 0.054 |
| SBI | 0.186 | 0.016 | 0.012 | 1.114 |
| DMX | 0.014 | 0.000 | 0.001 | 0.030 |
| Heavies | 0.134 | 0.051 | 0.050 | 0.270 |
| pp/op, Product | 8.303 | 10.123 | 11.366 | 8.151 |
| Productivity | 0.1862 | 0.1022 | 0.287 | 0.2508 |
| pp-BPA Selectivity | 79.16 | 86.90 | 88.40 | 70.56 |
| Acetone consumed | 3.18 | 3.05 | 4.20 | 5.18 |
| Acetone conversion | 63.66 | 61.07 | 84.01 | 103.57 |
| Selectivity overall | 88.70 | 95.49 | 96.17 | 79.22 |

Experiment 11 achieved a water concentration of 0.23% w/w. The general trend of decreasing water concentration was observed along the length of reactor. The p,p-BPA selectivity was impacted by reaction temperature. Experiment numbers 9, 11, 14 performed at higher temperature show increased concentration of non-isomerizable impurities CD-1 and SBI and low BPA selectivity. Acetone conversion is non-comparable with base case as material balance was not closed. Acetone consumed in experiment number 14 (inferred from product composition) is comparable to that in base case. This confirms that significant amount of acetone is available for reaction, even though acetone was stripped with nitrogen.

No profile was observed for p,p-BPA concentration along the length of reactor. A concentration profile for p,p-BPA was expected as acetone was feed along the length of reactor. Therefore, liquid phase back-mixing was suspected in this set of reactive stripping experiments.

In a packed bed reactor setup 80% of the acetone reacts in first 20% of the catalyst bed, increase in p,p-BPA concentration after that is lesser. For the base case experiments as the bottom stage sampling point is after ~30% of the catalyst bed, a concentration profile for p,p-BPA is not observed along the length of reactor. A finer sampling is required in the initial 30% catalyst bed to confirm the extent of back-mixing.

At gas flowrates higher than that used in the experiments slugs of gas formed, which disturbed and carried over the liquid phase while travelling from stages. Equal volume of liquid was seen displaced and trickled down to the bottom stage from the clearance at periphery of the horizontal baffles, when the gas slugs travelled from bottom stage to upper stage. This liquid phase recirculation was not so severe at the range of gas flowrates in this set of experiments; but might have contributed to the liquid back-mixing. Due to inert gas sparging, good mixing of solid phase was observed on each stage. The liquid circulation pattern was centrally up and peripherally down. Gas bubble size was in the range of 0.5-3 mm (visual observation). Gas pockets were observed below horizontal baffles, the maximum gas holdup was about 50% at highest gas flowrate.

Example 3. Bisphenol A Reactive Stripper Model

Example 3.1. Bisphenol A Reactor Column Model Development

A model was developed for BPA reactive stripping using Aspen Plus™ as a RADRFRAC block with equilibrium stages and user-defined reactive distillation kinetic subroutine. It was a stripping column, without condenser and reboiler in case of stripping with nitrogen; without condenser and with reboiler in case of stripping with vacuum. The total numbers of reactive stages were 14, with 4 non-reactive stages at the top. Stage 18 was the bottom stage, and stage 0 was the top stage. Due to inert gas sparging or vacuum, liquid temperature decreases at the exit, which decreases acetone conversion. Five heat streams were used to control the desired temperature on stages 4, 6, 10, 13 and 17. Catalyst volume (catalyst density 0.45 tons/m$^3$) on each stage was an input to the model. Phenol was stream fed to the column on stage 1, with the composition given in Table 4.

TABLE 4

Feed composition.

| Component | Unit | Composition |
|---|---|---|
| PHENOL | % w/w | 81.13586 |
| WATER | % w/w | 0.207373 |
| ACETONE | % w/w | 0 |
| 3-MPA | SH, ppm | 1300 |
| PP-BPA | % w/w | 11.46791 |
| OP-BPA | % w/w | 2.77649 |
| CHROMAN | % w/w | 0.846924 |
| DIMERS | % w/w | 0.6893 |
| BPX-I | % w/w | 0.511534 |
| BPX-II | % w/w | 0.889487 |
| HEAVIES | % w/w | 1.038805 |

Liquid phase Acetone fed to column was split into 3 streams and entered on stages 10 (33%), 12 (50%), and 14 (17%). Vapor phase acetone was fed to the column on single stage 14. Nitrogen was fed to the column on stage 18. Vacuum was introduced to the column on stage 1. Parameters selected for design of BPA reactive stripping column are given in Table 5.

TABLE 5

Design parameters for BPA reactor column.

| Parameter | Unit | Catalytic structured packing column | Alternate reaction zone, mass transfer zone with chimney | Sieve tray column |
|---|---|---|---|---|
| Number of reactive stages | No. | 14 | 14 | 14 |
| Number of non-reactive stages at top | No. | 4 | 4 | 4 |
| Number of separation stage | No. | — | 14 | — |
| Liquid Acetone feed location stage | No. | 10, 12, 14 | 28 | 10, 12, 14 |
| Heat stream input location stage | No. | 4, 6, 10, 13, 17 | — | 4, 6, 10, 13, 17 |
| Fractional approach to flooding |  | 0.6 | 0.6 | 0.3 |
| Reactive stages spacing/sieve Tray spacing | m | — | 1 | 1 |
| Non-reactive stages sieve Tray spacing | m | — | 0.5 | 0.5 |
| Weir height:tray spacing ratio | % | — | 15 | 50 |
| Packing type |  | KATAPAK ™ is Mellapack 750Y | KATAPAK ™ is Mellapack 750Y | — |
| Reactive stage Packing HETP | m | 1 | — | — |
| Non-reactive stage Packing HETP | m | 0.3 | 0.3 | — |
| Catalyst holdup per unit volume of packing or sieve tray liquid holdup | vol % | 30 | — | 30 | the packed column height was calculated as the height of the non-reactive stages plus ((total catalyst volume/maximum fractional catalyst loading)/cross sectional area of column. The alternate mass transfer reaction zone height was calculated as the height of mass transfer stages plus the height of non-reactive stages plus (total catalyst volume/cross sectional area of column). The sieve tray column number of trays was calculated as the number of non-reactive stages plus ((total catalyst volume/maximum fractional catalyst loading)/(cross sectional area of tray*weir height)). Height of mass transfer section was calculated based on HETP or tray spacing. Final height or number of trays of reactive stripping column is recommended to be highest of that required for reaction and mass transfer.

Example 3.2. Reactor Column Model

Steady state simulation model were developed using Aspen Plus™ for catalytic structured packing column as shown in FIG. 1A; alternate reactive zone (packed bed of IER catalyst) and separation zone column as shown in FIG. 1B, and sieve tray column as shown in FIG. 1C. These models are used for estimating optimized operating conditions and reactor sizes, and are described in Example 3.1.

Simulations were performed with water stripping by nitrogen or vacuum, with stage temperature controlled using heat streams or without temperature control (adiabatic operation), with acetone fed as liquid or vapor phase. Factors studied were space velocity, feed temperature, nitrogen flowrate, pressure, stage temperature, overall acetone concentration in feed, phase of acetone, and concentration of promoter in feed.

Optimized results for the different setups are given in Tables 6A-6E. Run 1 in Table 6 is with plug flow reactor operating at higher space velocity. Productivity, acetone conversion with this setup of reactor is lesser than stripping reactor arrangement.

TABLE 6A

Aspen Plus ™ model results for catalytic structured packing column with nitrogen stripping and liquid phase acetone feed.

| Factors | Unit | ASPEN Plug flow reactor | ASPEN Temperature control with heat streams | ASPEN Uncontrolled stage temperature | ASPEN Uncontrolled stage temperature, vapor phase acetone feed on stage 16 |
|---|---|---|---|---|---|
| Run |  | 1 | 2 | 3 | 4 |
| Feed flow | kg/hr | 39906.44 | 39906.44 | 38220.05 | 38220.05 |
| Feed flow, WHSV | hr$^{-1}$ | 6.60 | 6.60 | 5.52 | 5.52 |
| Feed temperature | ° C. | 55 | 55 | 70 | 55 |
| Overall Acetone concentration | % w/w | 5.28 | 5.28 | 5.49 | 5.49 |
| Acetone temperature | ° C. | 55 | 55 | 55 | 55 |
| Nitrogen/Feed ratio | m$^3$/kg | — | 0.48 | 0.48 | 0.48 |
| Nitrogen temperature | ° C. | — | 60 | 60 | 60 |
| Catalyst volume per stage | m3 | — | 0.96 | 1.1 | 1.1 |
| Temp stage 4 | ° C. | — | 85.00 | 80.85 | 74.77 |
| Temp stage 6 | ° C. | — | 85.00 | 82.96 | 75.32 |
| Temp stage 10 | ° C. | — | 75.40 | 87.25 | 76.99 |
| Temp stage 13 | ° C. | — | 76.01 | 83.27 | 82.32 |
| Temp stage 17 | ° C. | — | 74.28 | 76.79 | 80.85 |
| 3 MPA concentration in feed | SH ppm | 1300 | 1300.00 | 1300.00 | 1300.00 |

TABLE 6A-continued

Aspen Plus ™ model results for catalytic structured packing column with nitrogen stripping and liquid phase acetone feed.

| Factors | Unit | ASPEN | ASPEN | ASPEN | ASPEN |
|---|---|---|---|---|---|
| | | RESPONSES | | | |
| BPA production | KTA | 41.23 | 65.80 | 64.98 | 61.87 |
| BPA productivity | kg BPA/ kg IER · hr | 0.75 | 1.29 | 1.11 | 1.06 |
| BPA concentration in product | % w/w | 22.83 | 31.09 | 31.7 | 30.73 |
| op-BPA concentration in product | % w/w | 2.78 | 3.10 | 3.45 | 3.86 |
| Acetone conversion | % w/w | 59.18 | 94.89 | 94.61 | 90.82 |
| p,p-BPA selectivity | % | 98.8 | 97.97 | 96.23 | 94.19 |
| Acetone loss in exit gas | % w/w | — | 5.08 | 4.59 | 6.59 |
| Water in product % | % w/w | 1.15 | 0.02 | 0.12 | 0.15 |
| Packed Column diameter | m | — | 2.55 | 2.51 | 2.54 |
| Height of column based on reaction | m | — | 9.95 | 11.57 | 11.33 |
| Height of column based on separation | m | — | 15.2 | 15.2 | 15.2 |

TABLE 6B

Aspen Plus ™ model results for Alternate reaction zone and masstransfer zone column with sub atmospheric operation stripping and vapor phase acetone feed.

| Factors | Unit | ASPEN |
|---|---|---|
| | | Uncontrolled stage temperature, vapor phase acetone feed on stage 28 |
| Run | | 1 |
| Feed flow | kg/hr | 38220.05 |
| Feed flow, WHSV | hr$^{-1}$ | 5.52 |
| Feed temperature | ° C. | 55 |
| Overall Acetone concentration | % w/w | 5.49 |
| Acetone temperature | ° C. | 55 |
| Column top pressure | mmHg | 50 |
| Catalyst volume per stage | m3 | 1.1 |
| Temp stage 2 | ° C. | 68.78 |
| Temp stage 5 | ° C. | 69.18 |
| Temp stage 11 | ° C. | 70.63 |
| Temp stage 15 | ° C. | 72.35 |
| Temp stage 19 | ° C. | 75.35 |
| Temp stage 23 | ° C. | 79.06 |
| Temp stage 27 | ° C. | 77.30 |
| Temp stage 31 | ° C. | 79.76 |
| Temp stage 32 | ° C. | 90.63 |
| 3 MPA concentration in feed | SH ppm | 1300.00 |

TABLE 6B-continued

Aspen Plus ™ model results for Alternate reaction zone and masstransfer zone column with sub atmospheric operation stripping and vapor phase acetone feed.

| Factors | Unit | ASPEN |
|---|---|---|
| | RESPONSES | |
| BPA production | KTA | 61.87 |
| BPA productivity | kg BPA/ kg IER · hr | 1.06 |
| BPA concentration in product | % w/w | 27.52 |
| op-BPA concentration in product | % w/w | 3.39 |
| Acetone conversion | % w/w | 79.71 |
| p,p-BPA selectivity | % | 93.68 |
| Acetone loss in exit gas | % w/w | 1.23 |
| Water in product % | % w/w | 0.2 |
| Column diameter if structured packing used as separation zone | M | 1.87 |
| Column diameter if sieve tray used as separation zone | M | 1.58 |
| Height column including reaction and separation zone if structure packing used as separation zone | M | 10.96 |
| Height column including reaction and separation zone if sieve tray used as separation zone | M | 23.85 |

TABLE 6C

Aspen PlusTM model results for catalyst supported on sieve tray column with nitrogen stripping and liquid phase acetone feed.

| Factors | Unit | ASPEN | ASPEN | ASPEN |
|---|---|---|---|---|
| | | Temperature control with heat streams | Uncontrolled stage temperature | Uncontrolled stage temperature, vapor phase acetone feed on stage 16 |
| Run | | 1 | 2 | 3 |
| Feed flow | kg/hr | 42749.97 | 38220.05 | 38220.05 |
| Feed flow, WHSV | hr$^{-1}$ | 6.79 | 5.52 | 5.52 |
| Feed temperature | ° C. | 55 | 70 | 55 |
| Overall Acetone concentration | % w/w | 4.81 | 5.49 | 5.49 |
| Acetone temperature | ° C. | 55 | 55 | 55 |
| Nitrogen/Feed ratio | m3/kg | 0.49 | 0.48 | 0.48 |
| Nitrogen temperature | ° C. | 60 | 60 | 60 |
| Catalyst volume per stage | m3 | 1.00 | 1.1 | 1.1 |

TABLE 6C-continued

Aspen PlusTM model results for catalyst supported on sieve tray column with nitrogen stripping and liquid phase acetone feed.

| Factors | Unit | ASPEN | ASPEN | ASPEN |
|---|---|---|---|---|
| Temp stage 4 | ° C. | 80.32 | 80.85 | 74.77 |
| Temp stage 6 | ° C. | 83.29 | 82.96 | 75.32 |
| Temp stage 10 | ° C. | 84.03 | 87.25 | 76.99 |
| Temp stage 13 | ° C. | 73.00 | 83.27 | 82.32 |
| Temp stage 17 | ° C. | 73.00 | 76.79 | 80.85 |
| 3 MPA concentration in feed | SH ppm | 1300.00 | 1300.00 | 1300.00 |
| RESPONSES | | | | |
| BPA production | KTA | 65.50 | 64.98 | 61.87 |
| BPA productivity | kg BPA/ kg IER · hr | 1.24 | 1.12 | 1.06 |
| BPA concentration in product | % w/w | 29.70 | 31.7 | 30.73 |
| op-BPA concentration in product | % w/w | 2.92 | 3.45 | 3.86 |
| Acetone conversion | % w/w | 96.32 | 94.61 | 90.82 |
| p,p-BPA selectivity | % | 98.78 | 96.23 | 94.19 |
| Acetone loss in exit gas | % w/w | 3.65 | 4.59 | 6.59 |
| Water in product % | % w/w | 0.02 | 0.12 | 0.15 |
| Sieve tray column diameter | M | 3.18 | 3 | 3.04 |
| Number of tray based on reaction | Nos. | 17.02 | 19.72 | 19.72 |
| Number of tray based on separation | Nos. | 24 | 24 | 24 |

TABLE 6D

Aspen Plus ™ model results for catalytic structured packing column with sub-atmospheric operation stripping and vapor phase acetone feed.

| Factors | Unit | ASPEN | ASPEN | ASPEN | ASPEN |
|---|---|---|---|---|---|
| | | Uncontrolled stage temperature, vapor phase acetone feed stage16 | Uncontrolled stage temperature, vapor phase acetone feed on stage 14 | Uncontrolled stage temperature, vapor phase acetone feed stage16 | Uncontrolled stage temperature, liquid phase acetone feed stage14, 15, 16 |
| Run | | 1 | 2 | 3 | 4 |
| Feed flow | kg/hr | 38220.05 | 38220.05 | 38220.05 | 38220.05 |
| Feed flow, WHSV | hr$^{-1}$ | 5.52 | 5.52 | 5.52 | 5.52 |
| Feed temperature | ° C. | 55 | 55 | 50 | 55 |
| Overall Acetone concentration | % w/w | 5.49 | 5.49 | 5.49 | 5.49 |
| Acetone temperature | ° C. | 55 | 55 | 55 | 55 |
| Column top pressure | mmHg | 30 | 20 | 30 | 30 |
| Catalyst volume per stage | m$^3$ | 1.1 | 1.1 | 1.1 | 1.1 |
| Temp stage 4 | ° C. | 64 | 73.8 | 61.3 | 64.48 |
| Temp stage 6 | ° C. | 64.63 | 74.26 | 61.9 | 65.44 |
| Temp stage 10 | ° C. | 69.72 | 73.04 | 64.84 | 70.8 |
| Temp stage 13 | ° C. | 76.58 | 66.09 | 70.42 | 73.26 |
| Temp stage 17 | ° C. | 75.71 | 68.69 | 72.08 | 66.67 |
| Temp stage 18 | ° C. | 80.24 | 72.33 | 79.67 | 78.32 |
| 3 MPA concentration in feed | SH ppm | 1300.00 | 1300.00 | 1300.0 | 1300.0 |
| RESPONSES | | | | | |
| BPA production | KTA | 60.71 | 69.92 | 55.89 | 59.68 |
| BPA productivity | kg BPA/ kg IER · hr | 1.04 | 1.20 | 0.96 | 1.03 |
| BPA concentration in product | % w/w | 30.37 | 33.24 | 28.87 | 30.05 |
| op-BPA concentration in product | % w/w | 3.33 | 3.19 | 3.07 | 3.05 |
| Acetone conversion | % w/w | 90.55 | 94.47 | 82.88 | 85.86 |
| p,p-BPA selectivity | % | 96.59 | 98.22 | 97.24 | 98.11 |
| Acetone loss in vapor | % w/w | 6.71 | 4.47 | 13.29 | 7.9 |
| Water in product % | % w/w | 0.2 | 0.2 | 0.2 | 0.2 |
| Packed Column diameter | m | 2.13 | 2.62 | 2.04 | 2.02 |
| Height of column based on reaction | m | 15.61 | 10.72 | 16.91 | 17.2 |

TABLE 6D-continued

Aspen Plus ™ model results for catalytic structured packing column
with sub-atmospheric operation stripping and vapor phase acetone feed.

| Factors | Unit | ASPEN | ASPEN | ASPEN | ASPEN |
|---|---|---|---|---|---|
| Height of column based on separation | m | 15.2 | 15.2 | 15.2 | 15.2 |
| Reboiler duty | kw | 147.25 | 115.67 | 256.72 | 412 |

TABLE 6E

Aspen Plus ™ model results for catalyst supported on sieve tray
column with sub-atmospheric operation stripping and vapor phase acetone feed.

| Factors | Unit | ASPEN | ASPEN | ASPEN | ASPEN |
|---|---|---|---|---|---|
| | | Uncontrolled stage temperature, vapor phase acetone feed stage16 | Uncontrolled stage temperature, vapor phase acetone feed on stage 14 | Uncontrolled stage temperature, vapor phase acetone feed stage16 | Uncontrolled stage temperature, liquid phase acetone feed stage14, 15, 16 |
| Run | | 1 | 2 | 3 | 4 |
| Feed flow | kg/hr | 38220.05 | 38220.05 | 38220.05 | 38220.05 |
| Feed flow, WHSV | $hr^{-1}$ | 5.52 | 5.52 | 5.52 | 5.52 |
| Feed temperature | °C. | 55 | 55 | 50 | 55 |
| Overall Acetone concentration | % w/w | 5.49 | 5.49 | 5.49 | 5.49 |
| Acetone temperature | °C. | 55 | 55 | 55 | 55 |
| Nitrogen/Feed ratio | $m^3$/kg | 30 | 20 | 30 | 30 |
| Catalyst volume per stage | $m^3$ | 1.1 | 1.1 | 1.1 | 1.1 |
| Temp stage 4 | °C. | 64 | 73.8 | 61.3 | 64.48 |
| Temp stage 6 | °C. | 64.63 | 74.26 | 61.9 | 65.44 |
| Temp stage 10 | °C. | 69.72 | 73.04 | 64.84 | 70.8 |
| Temp stage 13 | °C. | 76.58 | 66.09 | 70.42 | 73.26 |
| Temp stage 17 | °C. | 75.71 | 68.69 | 72.08 | 66.67 |
| Temp stage 18 | SH ppm | 80.24 | 72.33 | 79.67 | 78.32 |
| 3 MPA concentration in feed | | 1300.00 | 1300.00 | 1300.0 | 1300.0 |
| RESPONSES | | | | | |
| BPA production | KTA | 60.71 | 69.92 | 55.89 | 59.68 |
| BPA productivity | kg BPA/ kg IER · hr | 1.04 | 1.20 | 0.96 | 1.03 |
| BPA concentration in product | % w/w | 30.37 | 33.24 | 28.87 | 30.05 |
| op-BPA concentration in product | % w/w | 3.33 | 3.19 | 3.07 | 3.05 |
| Acetone conversion | % w/w | 90.55 | 94.47 | 82.88 | 85.86 |
| p,p-BPA selectivity | % | 96.59 | 98.22 | 97.24 | 98.11 |
| Acetone loss in exit gas | % w/w | 6.71 | 4.47 | 13.29 | 7.9 |
| Water in product % | % w/w | 0.2 | 0.2 | 0.2 | 0.2 |
| Reboiler duty | KW | 147.25 | 115.67 | 256.7 | 412 |
| Sieve tray column diameter | m | 2.95 | 3.85 | 2.81 | 2.79 |
| Number of tray based on reaction | Nos. | 20.69 | 13.85 | 22.39 | 22.66 |
| Number of tray based on separation | Nos. | 24 | 24 | 24 | 24 |

Figure 4A:
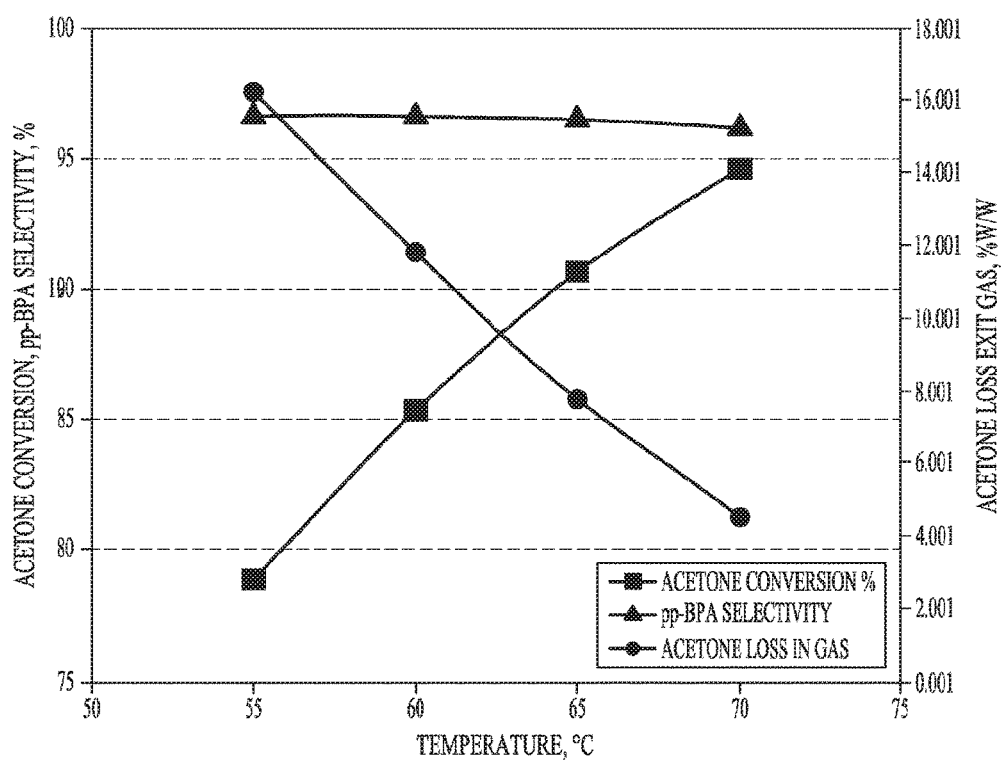
FIG. 4a illustrates acetone conversion, acetone loss, and bisphenol A selectivity versus liquid feed temperature.
Figure 4B:
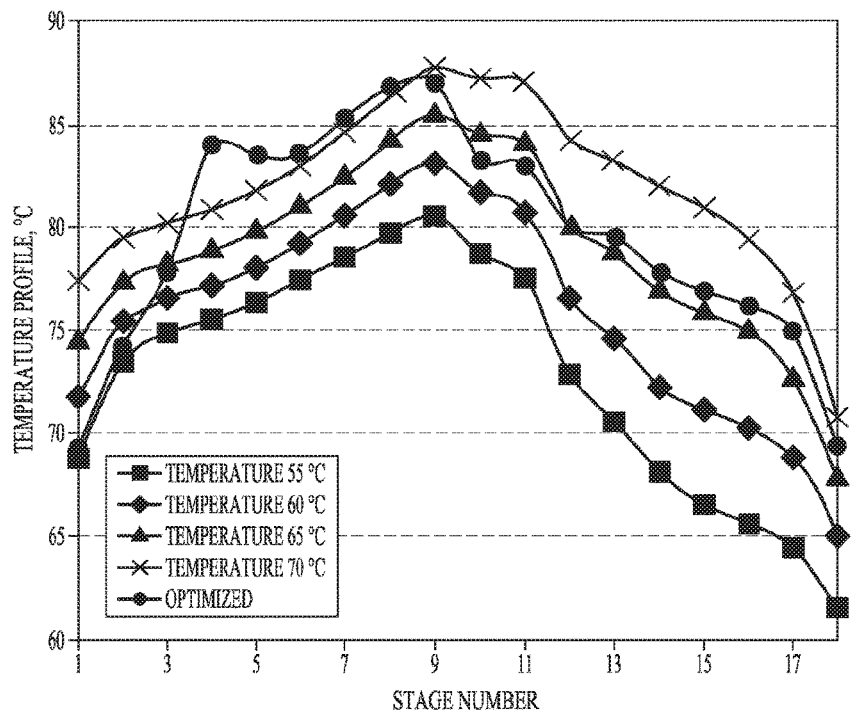
FIG. 4b illustrates a temperature profile of the reactor column for various liquid feed temperatures.
Figure 4C:
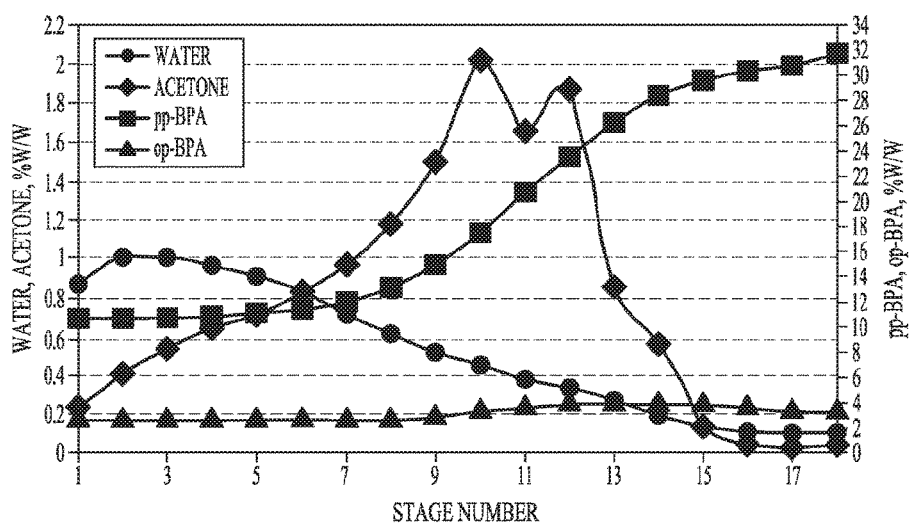
FIG. 4c illustrates the concentration profile of water, acetone, 4,4'-(propane-2,2-diyl)diphenol, and 2,4'-(propane-2,2-diyl)diphenol using a liquid feed temperature of 70° C.

For the adiabatic setup (uncontrolled stage temperature), introduction of inert gas resulted in decreased reactor temperature profile. In the non-adiabatic setups, to maintain desired reactor temperature profile, heat streams were introduced which made the reactor design more complicated. Reactor design with adiabatic operation (no intermediate heat stream introduction) was simpler. Liquid feed temperature was one of the parameters to control overall reactor temperature. Effects of liquid feed temperatures are shown in FIGS. 4a-c. Optimized reactor temperature was higher in middle section of reactor to take advantage of higher rate of reaction; whereas temperature was lower in bottom part of reactor to take advantage of thermal equilibrium for higher p,p-BPA selectivity. It can be observed that the optimized reactor temperature profile coincides with reactor temperature profile for liquid feed temperature of 65° C. in bottom part (stages 10-18) of the reactor and coincides with reactor temperature profile for liquid feed temperature of 70° C. in top part (stages 5-9) of reactor. Increasing liquid feed temperature increased average reactor temperature profile and hence increased acetone conversion. The acetone conversion was 94.61% w/w and p,p-BPA selectivity was 96.23% for liquid feed temperature of 70° C. without intermediate heat stream, which were similar for an optimized reactor temperature profile.

At the location of acetone feeding, acetone concentration in liquid phase was higher and the maximum concentration was about 2 wt %. The rate of increase of BPA concentration was higher in the area of acetone feeding. Water concentration in liquid phase was below 1 wt % and decreased towards the bottom of reactor.

The terms and expressions that have been employed are used as terms of description and not of limitation, and there is no intention in the use of such terms and expressions of excluding any equivalents of the features shown and described or portions thereof, but it is recognized that various modifications are possible within the scope of the embodiments of the present invention. Thus, it should be understood that although the present invention has been specifically disclosed by specific embodiments and optional features, modification and variation of the concepts herein disclosed may be resorted to by those of ordinary skill in the art, and that such modifications and variations are considered to be within the scope of embodiments of the present invention.

The following exemplary embodiments are provided, the numbering of which is not to be construed as designating levels of importance:

Embodiment 1 provides a method of making a bisphenol, the method comprising:

feeding the phenol at or proximate to the first end of a reactor column comprising a first end and a second end, the reactor column comprising a solid catalyst distributed in multiple locations between the first end and the second end of the reactor column; (for example, the phenol can be a substituted or unsubstituted phenol);

feeding the oxomethylene compound to the reactor column at a first location that is at or proximate the first end and at one or more additional locations between the first location and the second end of the reactor column wherein the oxomethylene compound has the structure $R^1$—C(O)—$R^2$, wherein $R^1$ and $R^2$ are each independently chosen from —H, halide, and a substituted or unsubstituted ($C_1$-$C_{10}$)hydrocarbyl, or $R^1$ and $R^2$ together form a substituted or unsubstituted ($C_1$-$C_{20}$)hydrocarbyl ring that comprises the —C(O)— of the oxomethylene compound;

contacting the phenol and the oxomethylene compound in the reactor column in the presence of the catalyst sufficiently to condense the phenol and oxomethylene compound to give a diphenolmethylene product and water;

removing at least some of the water from the reactor column by at least one of entraining the water in an inert gas and operating the reactor column under a vacuum; and removing a product composition comprising the diphenolmethylene product at or proximate to the second end of the reactor column, wherein the removing of the water is sufficient such that the product composition is about 5 wt % or less water.

Embodiment 2 provides the method of Embodiment 1, wherein the first end of the reactor column is a top end and the second end of the reactor column is a bottom end.

Embodiment 3 provides the method of any of the preceding Embodiments, wherein the second end of the reactor column is a top end and the second end of the reactor column is a bottom end.

Embodiment 4 provides the method of any of the preceding Embodiments, wherein the reactor column is at least one of a bubble column, a trayed column, and a column with structured packing.

Embodiment 5 provides the method of any of the preceding Embodiments, wherein the reactor column is at least one of a sectionalized slurry bubble column, a column comprising catalytic structured packing, and a column comprising sieve trays comprising the catalyst and other sieve trays not comprising the catalyst.

Embodiment 6 provides the method of any of the preceding Embodiments, wherein the product composition is about 2 wt % or less water, for example, wherein the product composition is about 0.01 wt % to about 2 wt % water.

Embodiment 7 provides the method of any of the preceding Embodiments, wherein about 5 wt % to about 50 wt % of the product composition is the diphenolmethylene product; for example, wherein about 8 wt % to about 35 wt % of the product composition is the diphenolmethylene product.

Embodiment 8 provides the method of any of the preceding Embodiments, further comprising subjecting the product composition to at least one of crystallization, distillation, desorption; for example, subjecting the product to melt-crystallization.

Embodiment 9 provides the method of any of the preceding Embodiments, further comprising purifying the product composition to provide the diphenolmethylene product at a purity of at least about 90 wt % without subjecting the product composition to dehydration.

Embodiment 10 provides the method of any of the preceding Embodiments, wherein in the product composition, the concentration of the diphenolmethylene product divided by the sum of the diphenolmethylene product and the concentration of all other side-products is about 50% to about 98%; for example, is about 70% to about 95%.

Embodiment 11 provides the method of any of the preceding Embodiments, wherein the conversion of the oxomethylene compound is about 30 wt % to about 100 wt %, for example, is about 45 wt % to about 100 wt %.

Embodiment 12 provides the method of any of the preceding Embodiments, wherein the method produces about 0.05 to about 5 kg (for example, about 0.1 to about 2 kg) of the diphenol methylene product per kg of the catalyst in the reactor column per hour of performance of the method.

Embodiment 13 provides the method of any of the preceding Embodiments, wherein a feed rate of the inert gas divided by a feed rate of the phenol and the oxomethylene compound is about 0.001 L/kg to about 3 L/kg, for example, about 0.01 L/kg to about 1 L/kg.

Embodiment 14 provides the method of any of the preceding Embodiments, wherein the reactor column has a holdup of the catalyst of about 10 vol % to about 80 vol %, for example, about 20 vol % to about 60 vol %.

Embodiment 15 provides the method of any of the preceding Embodiments, wherein the method produces about 1 to about 50,000 kg (for example, about 10 to about 1,000 kg) of the diphenolmethylene product per hour per $m^3$ of reactor column volume.

Embodiment 16 provides the method of any of the preceding Embodiments, further comprising feeding a promoter to the reactor column, wherein the phenol and the oxomethylene contact one another in the presence of the promoter.

Embodiment 17 provides the method of Embodiment 16, wherein the promoter comprises at least one of sulfur dichloride, sodium thiosulfate, hydrogen sulfide, iron sulfide, an alkanethiol, an arenethiol, a thioglycolic acid, a mercaptoalkanesulfonic acid, an alkali alkyl xanthate, a polymer-bound mercaptan promoter, 2-mercaptobenzothiazole, 2-mercaptoethylamine, and 3-mercaptopropionic acid; for example, the promotor is 3-mercaptopropionic acid.

Embodiment 18 provides the method any of the preceding Embodiments, wherein the inert gas has a velocity from one end of the reactor column to the other end of about 0.01 cm/sec to about 30 cm/sec, for example, about 0.1 cm/sec to about 10 cm/sec.

Embodiment 19 provides the method of any of the preceding Embodiments, wherein the inert gas is injected at or proximate to a bottom end of the reactor column, and wherein the inert gas is removed from the reactor column at or proximate to a top end of the reactor column.

Embodiment 20 provides the method of any of the preceding Embodiments, wherein the reactor column is operated under a vacuum of about 0.000,1 kPa to about 100 kPa.

Embodiment 21 provides the method of any of the preceding Embodiments, wherein the reactor column is operated with a weight hourly space velocity of about 0.1 $h^{-1}$ to about 30 $h^{-1}$, for example, a weight hourly space velocity of about 0.5 $h^{-1}$ to about 5 $h^{-1}$, or a weight hourly space velocity of about 5 $h^{-1}$ to about 20 $h^{-1}$.

Embodiment 22 provides the method of any of the preceding Embodiments, wherein the reactor column has a temperature profile chosen from isothermal, adiabatic, and a higher temperature at the first end and a lower temperature at the second end.

Embodiment 23 provides the method of any of the preceding Embodiments, wherein the catalyst is at least one chosen from a metal foam supported acid catalyst, a chelating resin, a sulfonated polystyrene resin, a sulfonated divinyl benzene polystyrene copolymer, a phenol-formaldehyde sulfonic acid resin, and a formaldehyde sulfonic acid resin, for example, the catalyst is an ion-exchange resin catalyst.

Embodiment 24 provides the method of any of the preceding Embodiments, wherein the phenol is substituted with 1, 2, 3, or 4 groups independently selected from ($C_1$-$C_{20}$) hydrocarbyl and halo, for example, wherein the phenol is substituted with 1, 2, 3, or 4 ($C_1$-$C_5$)alkyl groups.

Embodiment 25 provides the method of any of the preceding Embodiments, wherein the phenol is chosen from phenol, cresol, 2-isopropylphenol, and 2-phenylphenol.

Embodiment 26 provides the method of any of the preceding Embodiments, wherein the phenol is an unsubstituted hydroxybenzene.

Embodiment 27 provides the method of any of the preceding Embodiments, wherein $R^1$ and $R^2$ are each independently chosen from —H and ($C_1$-$C_{10}$)alkyl.

Embodiment 28 provides the method of any of the preceding Embodiments, wherein the oxomethylene compound is chosen from acetone, acetophenone, hexafluoroacetone, butanone, benzophenone, acetaldehyde, formaldehyde, substituted or unsubstituted cyclohexanone, and 3,3,5-trimethylcyclohexanone, for example, wherein the oxomethylene compound is acetone.

Embodiment 29 provides the method of any of the preceding Embodiments, wherein the diphenolmethylene is at least one chosen from bisphenol A (2,2-bis(4-hydroxyphenyl)propane), bisphenol AP (1,1-bis(4-hydroxyphenyl)-1-phenyl-ethane), bisphenol AF (2,2-bis(4-hydroxyphenyl) hexafluoropropane), bisphenol B (2,2-bis(4-hydroxyphenyl) butane), bisphenol BP (bis-(4-hydroxyphenyl) diphenylmethane), bisphenol C (2,2-bis(3-methyl-4-hydroxyphenyl) propane), bisphenol E (1,1-Bis(4-hydroxyphenyl)ethane), bisphenol F (bis(4-hydroxydiphenyl)methane), bisphenol G (2,2-bis(4-hydroxy-3-isopropyl-phenyl)propane), bisphenol PH (5,5'-(1-methylethyliden)-bis[1,1'-(bisphenyl)-2-ol]propane), bisphenol TMC (1,1-bis(4-hydroyphenyl)-3,3,5-trimethyl-cyclohexane), and bisphenol Z (1,1-bis(4-hydroxyphenyl)-cyclohexane).

Embodiment 45 provides the method of Embodiments 1-28, wherein the diphenolmethylene is bisphenol A (4,4'-(propane-2,2-diyl)diphenol).

Embodiment 46 provides the method of Embodiment 45, wherein in the product composition the ratio of the 4,4'-(propane-2,2-diyl)diphenol to 2,4'-(propane-2,2-diyl)diphenol is about 5 to about 30, for example, about 8 to about 15.

Embodiment 48 provides a method of making a bisphenol, the method comprising:

feeding phenol at or proximate to the top end of a reactor column comprising a top end and a bottom end, the reactor column comprising a solid catalyst distributed in multiple locations between the top end and bottom end of the reactor column, wherein the reactor column has a holdup of the catalyst of about 20 vol % to about 60 vol %;

feeding acetone to the reactor column at a first location that is at or proximate the top end and at one or more additional locations between the first location and the bottom end of the reactor column, wherein the reactor column is operated with a weight hourly space velocity of about 5 $h^{-1}$ to about 20 $h^{-1}$;

contacting the phenol and the acetone compound in the reactor column in the presence of the catalyst sufficiently to condense the phenol and acetone to give bisphenol A (4,4'-(propane-2,2-diyl)diphenol) and water;

removing at least some of the water from the reactor column by at least one of entraining the water in an inert gas injected at or proximate the bottom end of the reactor column and removed from the reactor column at or proximate to the top end of the reactor column, wherein a feed rate of the inert gas divided by the feed rate of the phenol and the acetone is about 0.01 L/kg to about 0.55 L/kg; and removing a product composition comprising the bisphenol A at or proximate to the bottom end of the reactor column, wherein the removing of the water is sufficient such that the product composition is about 2 wt % or less water, wherein about 8 wt % to about 35 wt % of the product composition is the bisphenol A, and in the product composition the concentration ratio of the bisphenol A divided by sum of the concentration of the bisphenol A and the concentration of all other side-products is about 70% to about 95%;

wherein the method produces about 0.1 to about 2 kg of the bisphenol A per kg of the catalyst in the reactor column per hour of performance of the method, and about 10 to about 1,000 kg of the bisphenol A per hour per $m^3$ of reactor column volume Embodiment 49 provides an apparatus for making a bisphenol, the apparatus comprising:

a reactor column comprising a first end and a second end, the reactor column comprising a solid catalyst distributed in multiple locations between the first end and the second end of the reactor column;

a phenol inlet at or proximate to the first end of the reactor column configured for feeding of a substituted or unsubstituted phenol;

a first oxomethylene inlet at or near the first end of the reactor column configured for feeding of an oxomethylene compound, wherein the oxomethylene compound has the structure $R^1$—C(O)—$R^2$, wherein $R^1$ and $R^2$ are each independently chosen from —H, halide, and a substituted or unsubstituted ($C_1$-$C_{10}$)hydrocarbyl, or $R^1$ and $R^2$ together form a substituted or unsubstituted ($C_1$-$C_{20}$)hydrocarbyl ring that comprises the —C(O)— of the oxomethylene compound;

one or more additional oxomethylene inlets between the first oxomethlyene inlet and the second end of the reactor column configured for feeding of the oxomethylene compound, wherein the reactor column is configured such that the phenol and the oxomethylene compound contact one another in the reactor column in the presence of the catalyst sufficiently to condense the phenol and oxomethylene compound to give a diphenolmethylene product and water; and a product outlet at or proximate to the second end of the reactor column configured for removing a product composition comprising the diphenolmethylene product, wherein the reactor column is configured to remove the water by at entraining the water in an inert gas and operating under a vacuum, wherein the removing of the water is sufficient such that the product composition is about 5 wt % or less water.

What is claimed is:

1. A method of making a bisphenol, the method comprising:
    feeding phenol at or proximate to a first end of a reactor column comprising a first end and a second end, the reactor column comprising a solid catalyst distributed in multiple locations between the first end and the second end of the reactor column, wherein the phenol is substituted or unsubstituted;
    feeding oxomethylene compound to the reactor column at a first location that is at or proximate the first end and at an additional location between the first location and the second end of the reactor column, wherein the oxomethylene compound has the structure $R^1$—C(O)—$R^2$, wherein $R^1$ and $R^2$ are each independently —H, halide, or a substituted or unsubstituted ($C_1$-$C_{10}$) hydrocarbyl, or $R^1$ and $R^2$ together form a substituted or unsubstituted ($C_1$-$C_{20}$)hydrocarbyl ring that comprises the —C(O)— of the oxomethylene compound;
    contacting the phenol and the oxomethylene compound in the reactor column in the presence of the catalyst sufficiently to condense the phenol and oxomethylene compound to give a bisphenol product and water;
    removing at least some of the water from the reactor column by at least one of entraining the water in an inert gas and operating the reactor column under a vacuum; and
    removing a product composition comprising the bisphenol product at or proximate to the second end of the reactor column, wherein the removing of the water is sufficient such that the product composition is about 5 wt % or less water;
    wherein the reactor column has a temperature profile comprising a higher temperature at the first end and a lower temperature at the second end.

2. The method of claim 1, wherein about 5 wt % to about 50 wt % of the product composition is the bisphenol product.

3. The method of claim 1, further comprising purifying the product composition to provide the bisphenol product at a purity of at least about 90 wt % without subjecting the product composition to dehydration.

4. The method of claim 1, wherein in the product composition, the concentration of the bisphenol product divided by the sum of the concentration of the bisphenol product and the concentration of all other side-products is about 50% to about 98%.

5. The method of claim 1, wherein the method produces about 0.05 to about 5 kg of the bisphenol product per kg of the catalyst in the reactor column per hour of performance of the method.

6. The method of claim 1, further comprising feeding the inert gas to the reactor column, wherein a feed rate of the inert gas divided by a feed rate of the phenol and the oxomethylene compound is about 0.001 L/kg to about 3 L/kg.

7. The method of claim 1, wherein the method produces about 1 to about 50,000 kg of the bisphenol product per hour per $m^3$ of reactor column volume.

8. The method of claim 1, further comprising feeding a promoter to the reactor column, wherein the phenol and the oxomethylene contact one another in the presence of the promoter.

9. The method of claim 1, further comprising feeding the inert gas to one end of the reactor column, wherein the inert gas travels from one end of the reactor column to the other end, wherein the inert gas has a velocity from one end of the reactor column to the other end of about 0.01 cm/sec to about 30 cm/sec.

10. The method of claim 1, wherein the inert gas is injected at or proximate to a bottom end of the reactor column, and wherein the inert gas is removed from the reactor column at or proximate to a top end of the reactor column.

11. The method of claim 1, wherein the reactor column is operated with a weight hourly space velocity of about 0.1 $h^{-1}$ to about 30 $h^{-1}$.

12. The method of claim 1, wherein the phenol is phenol, cresol, 2-isopropylphenol, or 2-phenylphenol.

13. The method of claim 1, wherein the phenol is an unsubstituted hydroxybenzene.

14. The method of claim 1, wherein the oxomethylene compound is acetone, acetophenone, hexafluoroacetone, butanone, benzophenone, acetaldehyde, formaldehyde, substituted or unsubstituted cyclohexanone, or 3,3,5-trimethylcyclohexanone.

15. The method of claim 1, wherein the oxomethylene compound is acetone.

16. The method of claim 1, wherein the bisphenol is at least one selected from the group consisting of: bisphenol A (2,2-bis(4-hydroxyphenyl)propane), bisphenol AP (1,1-bis(4-hydroxyphenyl)-1-phenyl-ethane), bisphenol AF (2,2-bis(4-hydroxyphenyl)hexafluoropropane), bisphenol B (2,2-bis(4-hydroxyphenyl)butane), bisphenol BP (bis-(4-hydroxyphenyl) diphenylmethane), bisphenol C (2,2-bis(3-methyl-4-hydroxyphenyl)propane), bisphenol E (1,1-Bis(4-hydroxyphenyl)ethane), bisphenol F (bis(4-hydroxydiphenyl)methane), bisphenol G (2,2-bis(4-hydroxy-3-isopropyl-phenyl)propane), bisphenol PH (5,5'-(1-methylethyliden)-bis[1,1'-(bisphenyl)-2-ol]propane), bisphenol TMC (1,1-bis(4-hydroyphenyl)-3,3,5-trimethylcyclohexane), and bisphenol Z (1,1-bis(4-hydroxyphenyl)-cyclohexane).

17. The method of claim 1, wherein the bisphenol is bisphenol A (4,4'-(propane-2,2-diyl)diphenol).

18. The method of claim 1,
    wherein the first end is a top end of a reactor column and the second end is a bottom end,
    wherein the reactor column has a holdup of the catalyst of about 20 vol % to about 60 vol %;
    wherein the oxomethylene compound comprises acetone which is fed to the reactor column at a first location that is at or proximate the top end and at an additional location between the first location and the bottom end of the reactor column, wherein the reactor column is operated with a weight hourly space velocity of about 5 $h^{-1}$ to about 20 $h^{-1}$;
    wherein the bisphenol product is bisphenol A (4,4'-(propane-2,2-diyl)diphenol);

wherein the water is removed from the reactor column by at least one of entraining the water in an inert gas injected at or proximate the bottom end of the reactor column and removed from the reactor column at or proximate to the top end of the reactor column, wherein a feed rate of the inert gas divided by the feed rate of the phenol and the acetone is about 0.01 L/kg to about 0.55 L/kg, wherein the removing of the water is sufficient such that the product composition is about 2 wt % or less water; and wherein the product composition comprising the bisphenol A is removed at or proximate to the bottom end, wherein about 8 wt % to about 35 wt % of the product composition is the bisphenol A, and in the product composition the concentration ratio of the bisphenol A divided by sum of the concentration of the bisphenol A and the concentration of all other side-products is about 70% to about 95%;

wherein the method produces about 0.1 to about 2 kg of the bisphenol A per kg of the catalyst in the reactor column per hour of performance of the method, and about 10 to about 1,000 kg of the bisphenol A per hour per $m^3$ of reactor column volume.

* * * * *